United States Patent
Yao et al.

(10) Patent No.: US 11,964,962 B2
(45) Date of Patent: Apr. 23, 2024

(54) SUBSTITUTED PYRIDAZINONE COMPOUND AND USE THEREOF

(71) Applicant: SHANDONG FIRST MEDICAL UNIVERSITY & SHANDONG ACADEMY OF MEDICAL SCIENCES, Ji'nan (CN)

(72) Inventors: Qingqiang Yao, Ji'nan (CN); Weilin Xie, Ji'nan (CN); Véronique Plantevin Krenitsky, Ji'nan (CN); Bo Liu, Ji'nan (CN); Yan Li, Ji'nan (CN); Ying Zhi, Ji'nan (CN); Ying Li, Ji'nan (CN); Yanling Mu, Ji'nan (CN); Jingyong Sun, Ji'nan (CN); Haiyang Wang, Ji'nan (CN); Zhongyu Wu, Ji'nan (CN); Haijiao Chen, Ji'nan (CN); Tiandi Ding, Ji'nan (CN); Yue Wang, Ji'nan (CN); Haoyi Sun, Ji'nan (CN); Feipeng Zhang, Ji'nan (CN); Peng Meng, Ji'nan (CN); Qingxu Liu, Ji'nan (CN); Huajie Li, Ji'nan (CN); Yige Wang, Ji'nan (CN); Shanshan Wen, Ji'nan (CN)

(73) Assignee: SHANDONG FIRST MEDICAL UNIVERSITY & SHANDONG ACADEMY OF MEDICAL SCIENCES, Ji'nan (CN)

( * ) Notice: Subject to any disclaimer, the term of this patent is extended or adjusted under 35 U.S.C. 154(b) by 0 days.

(21) Appl. No.: 17/922,797

(22) PCT Filed: Dec. 14, 2021

(86) PCT No.: PCT/CN2021/137854
§ 371 (c)(1),
(2) Date: Nov. 2, 2022

(87) PCT Pub. No.: WO2022/127779
PCT Pub. Date: Jun. 23, 2022

(65) Prior Publication Data
US 2023/0167091 A1 Jun. 1, 2023

(30) Foreign Application Priority Data
Dec. 17, 2020 (CN) .......................... 202011501355.0

(51) Int. Cl.
*C07D 403/12* (2006.01)
*C07D 401/12* (2006.01)

(52) U.S. Cl.
CPC ......... *C07D 403/12* (2013.01); *C07D 401/12* (2013.01)

(58) Field of Classification Search
CPC .................................................. C07D 403/12
See application file for complete search history.

(56) References Cited

U.S. PATENT DOCUMENTS

2007/0032494 A1* 2/2007 Haynes ............... A61P 1/16
544/239

FOREIGN PATENT DOCUMENTS

| CN | 101228135 A | 7/2008 | | |
|---|---|---|---|---|
| CN | 101801960 A | 8/2010 | | |
| CN | 109574995 B | 7/2020 | | |
| CN | 111592528 A | 8/2020 | | |
| CN | 111646979 A | 9/2020 | | |
| CN | 111801324 A | 10/2020 | | |
| CN | 111909137 A | 11/2020 | | |
| CN | 112409340 A | 2/2021 | | |
| CN | 112645936 A | 4/2021 | | |
| EP | 3632898 A1 | 4/2020 | | |
| WO | WO-2019240938 A1 | * | 12/2019 | ............. A61K 31/53 |
| WO | 2020073974 A1 | 4/2020 | | |
| WO | 2020227549 A1 | 11/2020 | | |

OTHER PUBLICATIONS

Stella et al. Drug Delivery Systems, Characteristics & Biomedical Applications, 1980; pp. 111-176.*
Martha J. Kelly, et al., Discovery of 2-[3,5-Dichloro-4-(5-isopropyl-6-oxo-1,6-dihydropyridazin-3-yloxy)phenyl]-3,5-dioxo-2,3,4,5-tetrahydro[1,2,4]triazine-6-carbonitrile (MGL-3196), a Highly Selective Thyroid Hormone Receptor β Agonist in Clinical Trials for the Treatment of Dyslipidemia, Journal of Medicinal Chemistry, 2014, pp. 3912-3923, vol. 57.

* cited by examiner

*Primary Examiner* — Samira J Jean-Louis
(74) *Attorney, Agent, or Firm* — Bayramoglu Law Offices LLC

(57) ABSTRACT

Disclosed is a pyridazinone compound represented by Formula (I),

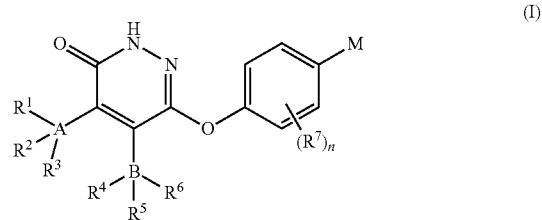

or a pharmaceutically acceptable salt, prodrug, hydrate, solvate, polymorph, stereoisomer, or isotopic variant thereof. The compound can be used for preparation of medicinal products for treatment and/or prophylaxis of a disease or condition associated with thyroid hormone abnormalities. The compound has higher selectivity to THβ, better pharmacokinetic parameters, desired stability, and higher agonistic activity toward THβ.

2 Claims, No Drawings

SUBSTITUTED PYRIDAZINONE COMPOUND AND USE THEREOF

CROSS REFERENCE TO THE RELATED APPLICATIONS

This application is the national phase entry of International Application No. PCT/CN2021/137854, filed on Dec. 14, 2021, which is based upon and claims priority to Chinese Patent Application No. 202011501355.0, filed on Dec. 17, 2020, the entire contents of which are incorporated herein by reference.

TECHNICAL FIELD

The present disclosure is related to the field of pharmaceutical technology, and in particular to a pyridazinone compound, its preparation and its pharmaceutical use as well as a pharmaceutical composition comprising the compound.

BACKGROUND

Generally, thyroid hormone (TH) is produced by the thyroid gland and is secreted into the circulatory system in two different forms: 3,5,3',5'-tetrakis-iodine-L-thyronine (T4) and 3,5,3'-Tri-iodo-L-thyronine (T3). T3 plays a major role in normal physiology.

The biological activity of THs is mediated by thyroid hormone receptors (TRs). TR belongs to a nuclear receptor superfamily, and there are two major subtypes of TRs, TRα and TRβ. Human TRs are encoded by the TRα and TRβ genes, located on human chromosomes 17 and 3, respectively, and yield a series of distinct isoforms through alternative splicing of primary transcripts. There are many TR isoforms that have been found, including TRα1, TRα2, TRα3, TRβ1, TRβ2, and TRβ3. Among these isoforms, TRα1, TRβ1, TRβ2, and TRβ3 can bind T3. The TR subtypes have been shown to differ in their contribution to specific physiological responses. TRα is highly expressed in the heart and skeletal muscle and plays a major role in regulating heart rate, whereas TRβ is highly expressed in liver, kidney, and pituitary gland and plays a major role in the regulation of thyroid stimulating hormone (TSH).

Too high or too low TH levels can severely influence metabolic balance of the body. In addition, it has been shown that THs have an effect of reducing cholesterol levels, ameliorating blood lipid levels, and treating obesity. It has been further reported that there is a significant negative correlation between free TH levels and each of the followings: cholesterol or triglyceride amount in the blood, blood pressure, obesity, and insulin resistance, which indicates that subjects with high free TH levels are at low risk for metabolic syndrome and if the subjects suffer from type 2 diabetes mellitus and are obese, the high TH levels in their body can help control blood sugar. By contrast, endogenous THs are nonselective, and a too high endogenous TH level produces undesirable side effects on muscles and bones, particularly cardiac stimulation, thereby limiting their applications in clinics. TRβ-selective agonists have the beneficial effects of TH including amelioration of blood lipid levels, reduction of low-density lipoprotein (LDL) cholesterol levels, increase in reuptake of high density lipoprotein (HDL) cholesterol, and reduction of plasma triglyceride levels, and have no the side-effects including increased heart rate. The development of TRβ-selective agonists that avoid the adverse effects of hyperthyroidism and hypothyroidism while maintaining the beneficial effects of THs will open new avenues for patients with the following diseases: non-alcoholic steatohepatitis (NASH), obesity, atherosclerosis, hyperlipidemia, hypercholesteremia, diabetes mellitus, and other conditions and diseases such as atherosclerosis, cardiovascular disease, hypothyroidism, thyroid cancer, thyroid disease, and related disorders and diseases.

Resmetirom (MGL-3196) is a selective TRβ agonist designed to improve NASH or NAFLD (non-alcoholic fatty liver disease), and is today in clinical phase 3 to evaluate the effectiveness and safety thereof in NASH or NAFLD patients. MGL-3196 is seen as one of the most promising drugs for treating NASH and NAFLD.

A pyridazinone compound which is structurally different from the compound of the present disclosure has been previously disclosed (Martha J. Kelly et al., *J. Med. Chem.*, vol. 57: pp. 3912-3923 (2014); Chinese Patent Applications CN 101228135 A (2008), CN 101801960 A (2010), CN 111646979 A (2020), CN 109574995 (2020), and CN 111592528 A).

Although MGL-3196 as a TRβ agonist is effective for the treatment of a variety of diseases, it is still a challenge to find a new compound that has better selectivity, low toxicity, and the beneficial effects of THs while avoiding the adverse effects and also has good oral bioavailability and druggability. Therefore, there is still a need in the art to develop highly potent and low-toxic TRβ-selective agonists with better specificity/pharmacodynamics/pharmacokinetic properties.

SUMMARY

In view of the above problems, among the objectives of the present disclosure are to provide a substituted pyridazinone compound or a pharmaceutically acceptable salt thereof and its preparation as well as a pharmaceutical composition and use of the compound or a pharmaceutically acceptable salt thereof for preparation of medicinal products for treatment and/or prophylaxis of a disease or condition associated with thyroid hormone abnormalities.

A first aspect of the present disclosure provides a compound of Formula (I) or a pharmaceutically acceptable salt thereof:

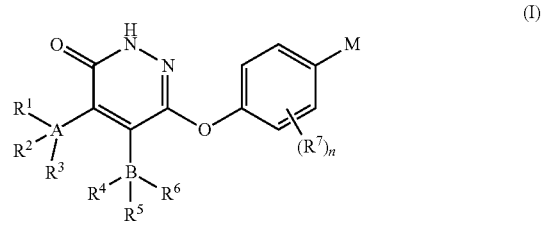

in which

R$^1$, R$^2$, and R$^3$ each independently represents a hydrogen atom or a straight or branched alkyl group having 1 to 4 carbon atoms;

A represents a hydrogen atom or a carbon atom;

R$^4$, R$^5$, and R$^6$ each independently represents a hydrogen atom or a straight or branched alkyl group having 1 to 4 carbon atoms;

$R^7$ represents a halogen atom or an alkoxy group which is methoxy or ethoxy, n=1 or 2;

M represents

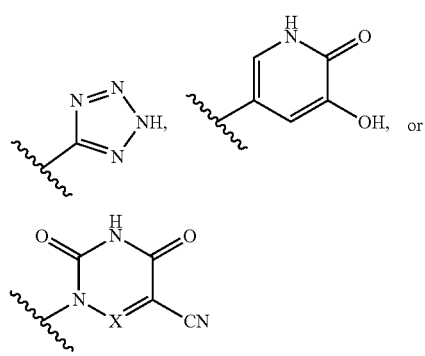

in which X represents N or CH;

$R^1$ or $R^2$ represents a cycloalkyl group having 3 to 5 carbon atoms when A represents a carbon atom; and $R^4$ or $R^5$ represents a cycloalkyl group having 3 to 5 carbon atoms when B represents a carbon atom.

The compound of Formula (I) may be selected from the group consisting of the following compounds 1 to 50, or a pharmaceutically acceptable salt, prodrug, hydrate, solvate, polymorph, stereoisomer, or isotopic variant thereof:

1

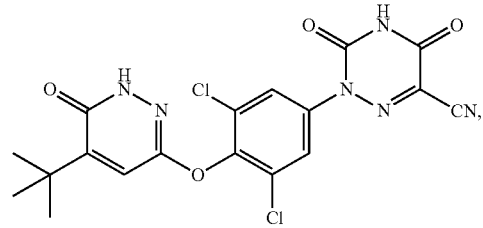

2

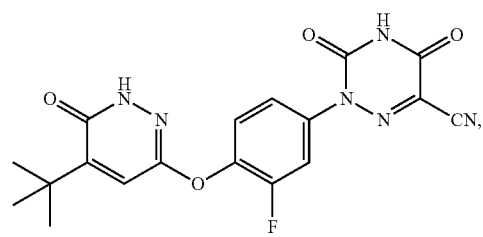

3

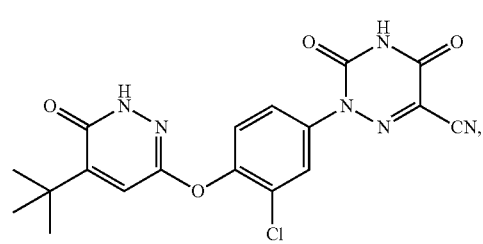

4

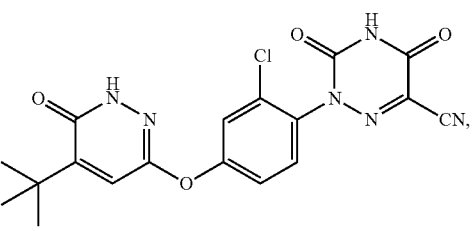

5

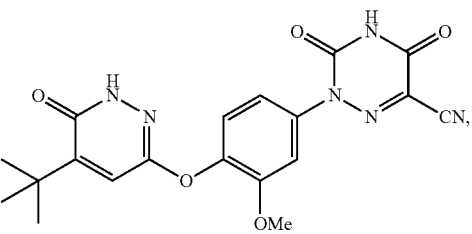

6

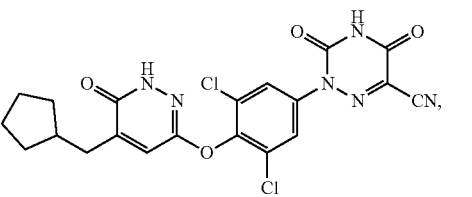

7

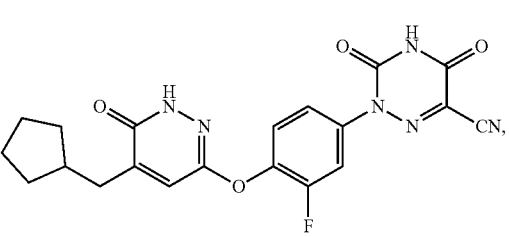

8

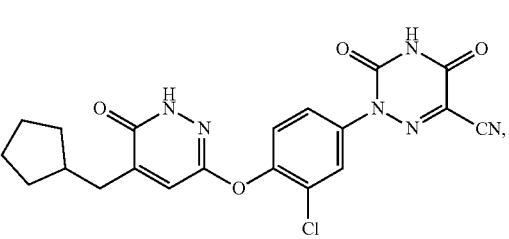

9

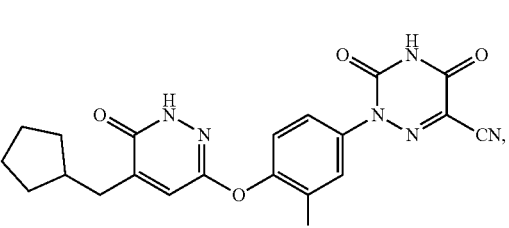

10

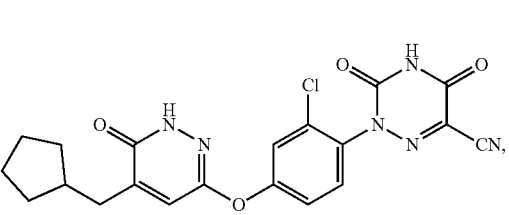

-continued

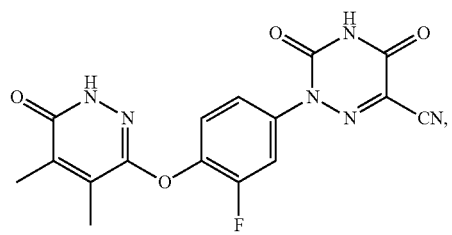
23
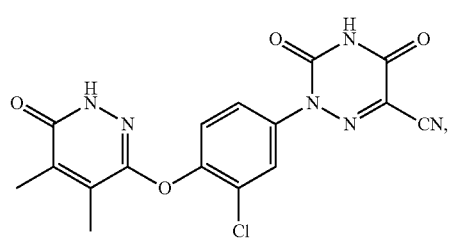
24
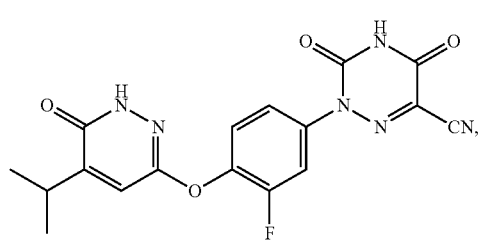
25
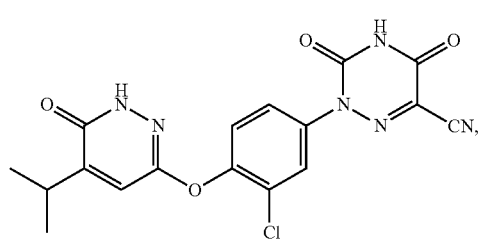
26
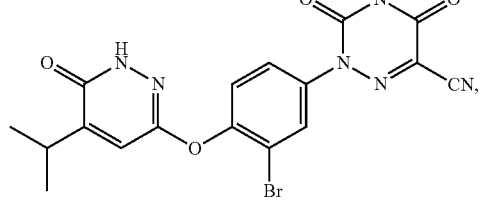
27
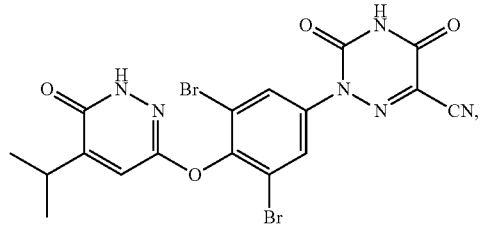
28
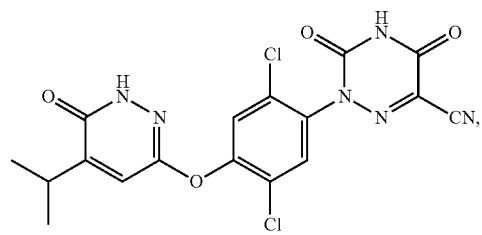
29
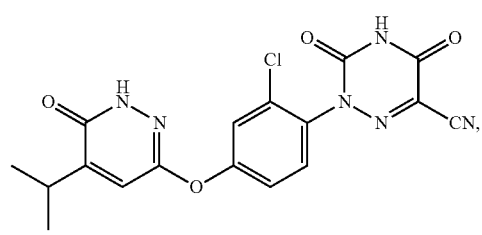
30
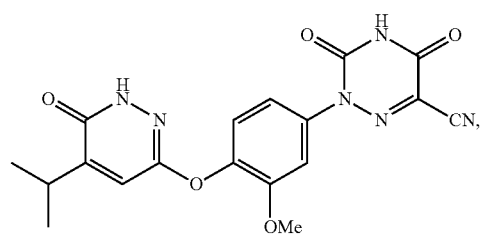
31
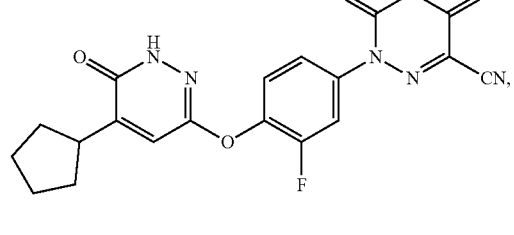
32
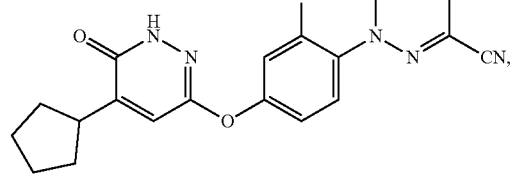
33
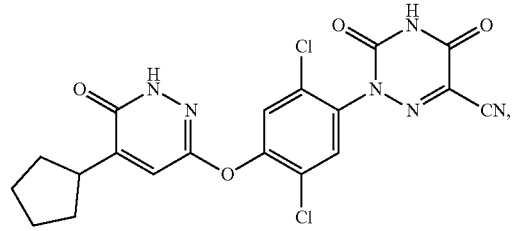
34

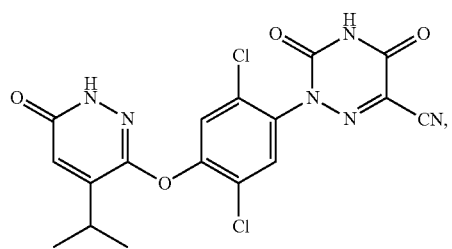
35
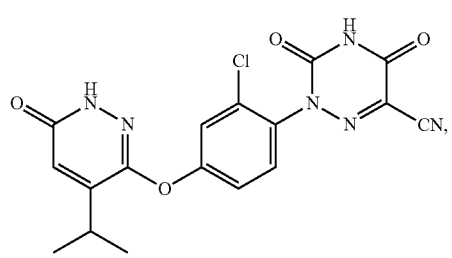
36
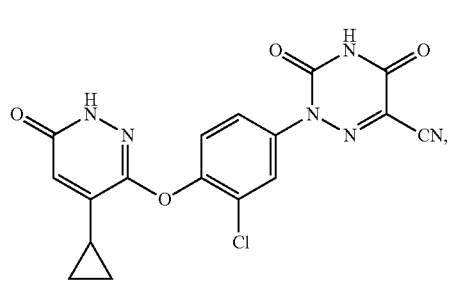
37
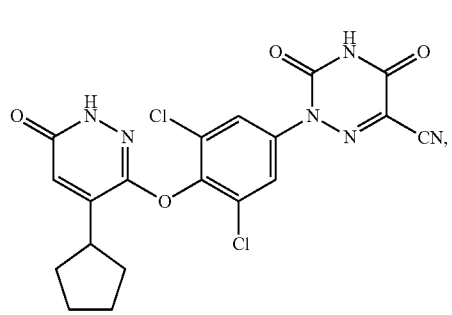
38
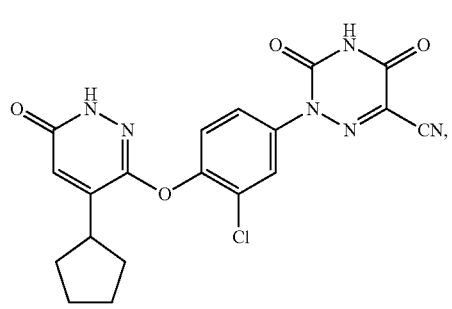
39
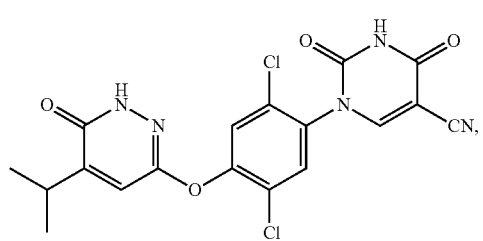
40
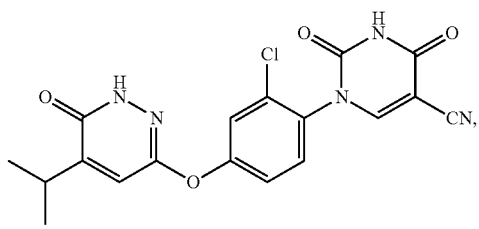
41
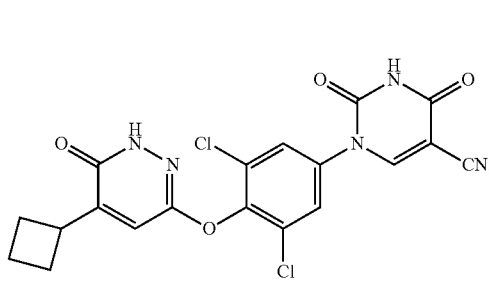
42
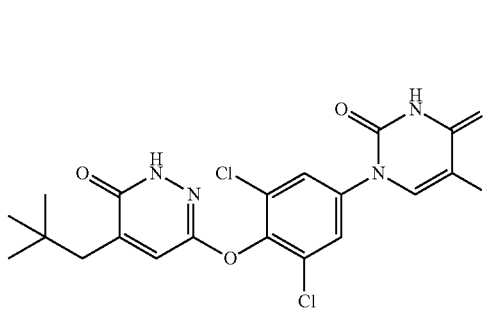
43
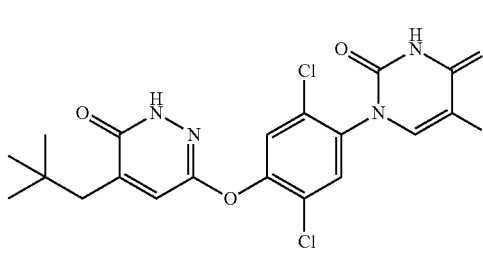
44
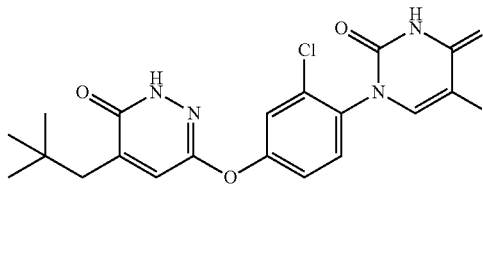
45
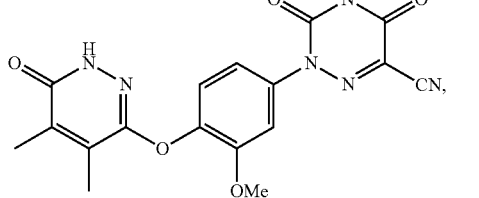
46

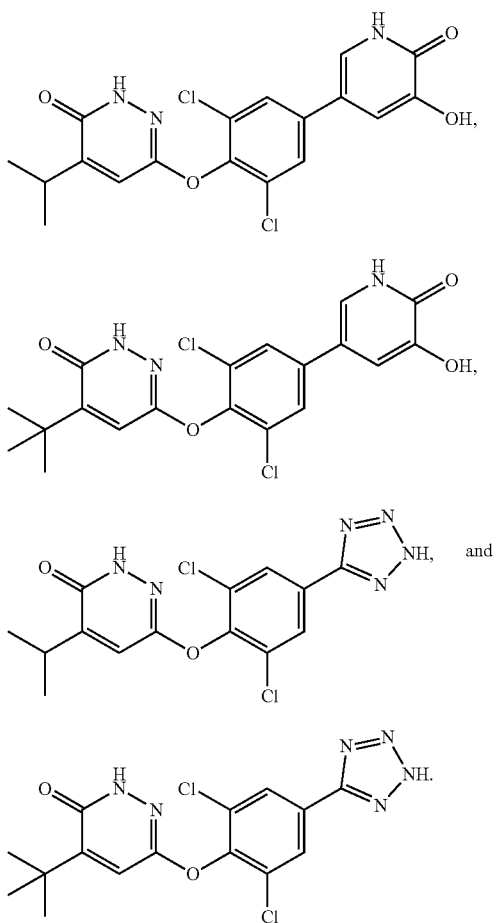

A second aspect of the present disclosure provides a thyroid hormone receptor-β (TRβ) agonist comprising an effective amount of the compound of Formula (I), or a pharmaceutically acceptable salt, stereoisomer, tautomer, resonance hybrid, enantiomer, diastereomer, hydrate, solvate, or polymorph thereof, as an active ingredient.

A third aspect of the disclosure provides a pharmaceutical composition comprising the compound of Formula (I) or a pharmaceutically acceptable salt thereof and a pharmaceutically-acceptable carrier or excipient. The pharmaceutical composition may be a clinically or pharmaceutically suitable dosage form, preferably an oral dosage form or an injectable dosage form. Exemplary dosage forms can contain a physiologically effective amount, which is generally in the range of 0.01 to 10 g per unit dosage form, such as 0.01 g, 0.015 g, 0.02 g, 0.025 g, 0.03 g, 0.04 g, 0.05 g, 0.1 g, 0.125 g, 0.2 g, 0.25 g, 0.3 g, 0.4 g, 0.5 g, 0.6 g, 0.75 g, 1 g, 1.25 g, 1.5 g, 1.75 g, 2 g, 2.5 g, 3 g, 4 g, 5 g, 6 g, 7 g, 8 g, 9 g, and 10 g, of the compound of Formula (I) or a pharmaceutically acceptable salt thereof.

The compounds of Formula (I) or a pharmaceutically acceptable salt thereof may be administered to a patient in need of such a treatment by oral, parenteral or other route of administration.

For parenteral administration, the compounds of Formula (I) or a pharmaceutically acceptable salt thereof may be formulated into injectable preparations including injections, sterile powders for injection, and concentrated solutions for injection. The injections may be packaged at a volume of 1 mL, 2 mL, 5 mL, 10 mL, 20 mL, 50 mL, 100 mL, 200 mL, 250 mL, and 500 mL. The sterile powders for injection are typically a sterile powder or cake to be dissolved in a sterilized solution to form a clear solution or a uniform suspension for injection before use. The sterile powders may be prepared through solvent crystallization, spray drying, or freeze drying. The concentrated solutions for injection are sterile concentrated solutions that are administered by intravenous infusion only after dilution.

These injectable preparations may be produced by any conventional process known to those skilled in the art using an aqueous solvent or a non-aqueous solvent. Traditionally, the most commonly used aqueous solvent is water for injection, but it is also possible to use a 0.9% sodium chloride solution or any other suitable aqueous solvent including, but not limited to: an aqueous ethanol solution, an aqueous solution of propylene glycol, and an aqueous solution of polyethylene glycol. A common example of the non-aqueous solvent is a vegetable oil, preferably soybean oil for injection. An additive may not be added, but according to the properties of those injectable forms to be produced, it is also possible to add one or more suitable additives including, but not limited to: osmolarity regulators, pH modifiers, solubilizers, fillers, antioxidants, bacteriostatic agents, emulsifiers, and suspending agents.

For oral administration the compounds of Formula (I) or a pharmaceutically acceptable salt thereof may be formulated into solid preparations such as tablets, capsules, pills, and powders, or liquid preparations such as solutions, suspensions, and syrups.

To produce these preparations suitable for oral administration, a suitable additive may be added, which includes, but is not limited to: fillers, binders, disintegrants, and lubricants. Common examples of the fillers are starch, powdered sugar, calcium phosphate, calcium sulfate dihydrate, dextrin, microcrystalline cellulose, lactose, pregelatinized starch, and mannitol.

The compounds of Formula (I) may be mixed with a pharmaceutically acceptable carrier to produce pharmaceutical preparations in the form of tablets, capsules, powders, syrups, solutions, suspensions, injections, etc. A pharmaceutically acceptable adjuvant such as flavors, sweeteners, solid or liquid fillers, and solid or liquid diluents, may also be added.

The compounds of Formula (I) may be administered through injection or oral administration or any other suitable means.

For the compounds of Formula (I), doses in the range of 0.01 to 1000 mg/day may be provided. However, the doses may also be out of the range depending on the severity of the condition and the different dosage forms.

A fourth aspect of the present disclosure provides use of the compounds of Formula (I) or a pharmaceutically acceptable salt thereof for preparation of medicinal products for treatment and/or prophylaxis of a disease or condition associated with thyroid hormone abnormalities. Examples of such a disease or condition include NASH, NAFLD, atherosclerosis, obesity, hyperlipidemia, hypercholesterolemia, diabetes, cardiovascular diseases, hypothyroidism, and cancer.

The compounds of the disclosure provides several advantages over prior art pyridazinone compounds, including:
1) higher selectivity to THβ;
2) better pharmacokinetic parameters and desired stability; and
3) higher agonistic activity toward THβ.

DETAILED DESCRIPTION OF THE EMBODIMENTS

The substituted pyridazinone compounds of the present disclosure or a pharmaceutically acceptable salt thereof will now be described in further detail.

The compounds of the present disclosure or a pharmaceutically acceptable salt, prodrug, hydrate, solvate, polymorph, stereoisomer, or isotopic variant thereof were prepared in the following examples.

Example 1—Synthesis of 2-(4-((5-(tert-butyl)-6-oxo-1,6-dihydropyridazin-3-yl)oxy)-3,5-dichlorophenyl)-3,5-dioxo-2,3,4,5-tetrahydro-1,2,4-triazine-6-carbonitrile (1)

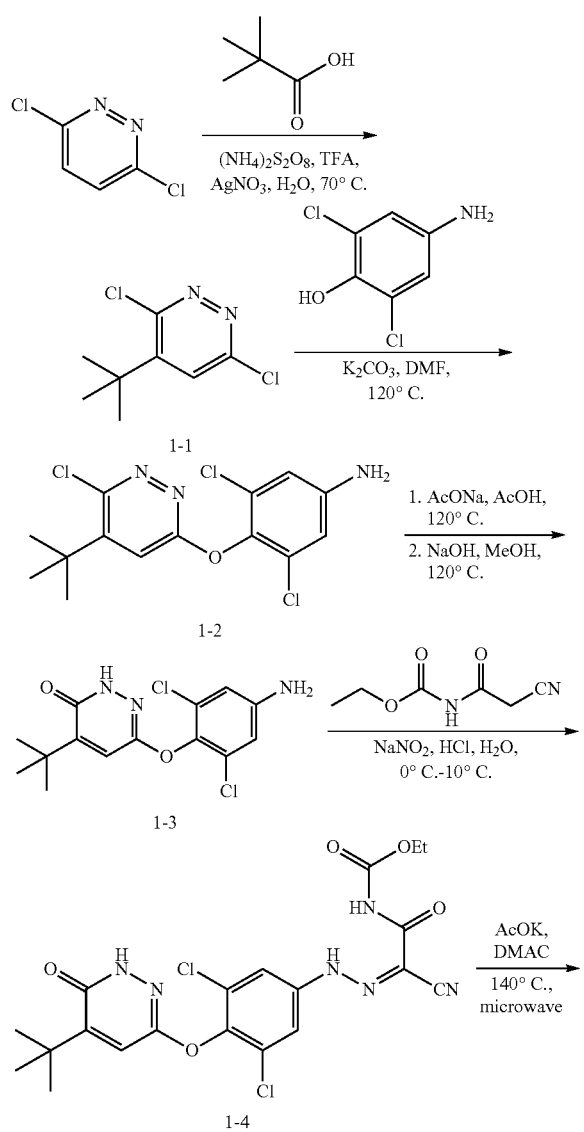

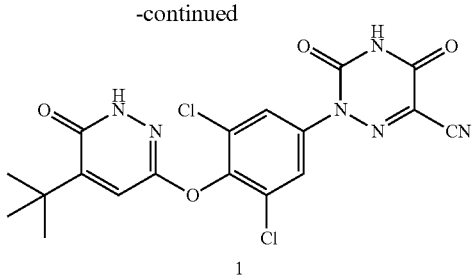

1

1) Synthesis of 4-(tert-butyl)-3,6-dichloropyridazine (1-1)

3,6-dichloropyridazine (14.9 g, 0.1 mol), pivalic Acid (20.4 g, 0.2 mol), purified water (300 mL), and trifluoroacetic acid (TFA, 7.4 mL, 0.1 mol) were added into a 1 L round-bottom flask and heated to 70° C. Silver nitrate (3.4 g, 0.2 mol) was then added. Next, ammonium persulfate aqueous solution (prepared by dissolving 91.3 g of solid ammonium persulfate in 200 mL of water) was added dropwise. The mixture was reacted at 70° C. for 30 min. Thin layer chromatography (TLC) indicated that the reaction was complete, and the reaction was stopped. Then, after the reaction mixture was cooled to room temperature, a concentrated solution of ammonia was added to adjust a pH to 9-10. The mixture was extracted with ethyl acetate (200 mL×3) and the combined organic phases were washed with saturated sodium chloride solution, dried over anhydrous sodium sulfate and then concentrated under reduced pressure to yield compound 1-1 as a colorless liquid (14.0 g, 56.5% yield). LRMS for $C_8H_{11}Cl_2N_2$ $(M+H)^+$ m/z=205.0, in agreement with the calculated value from ChemDraw: MW=205.0820, Exact mass=204.0221.

2) Synthesis of 4-((5-(tert-butyl)-6-chloropyridazin-3-yl)oxy)-3,5-dichloroaniline (1-2)

The compound 1-1 (0.82 g, 4.0 mmol) obtained in (1) above, 2,6-dichloro-4-aminophenol (0.71 g, 4.0 mmol), and potassium carbonate (1.10 g, 8.0 mmol) were added into a 100 mL round-bottom flask and reacted in N,N-Dimethylformamide (DMF, 10 mL) as a solvent at 120° C. for 3 h. TLC indicated that the reaction was complete, and the reaction was stopped. Then, after being cooled to room temperature, the reaction mixture was subjected to suction filtration by Celite which had been loaded into a glass-fritted funnel. The filter cake was rinsed with several sequential rinses of ethyl acetate. The filtrate and rinse were combined and washed with 10% aqueous sodium chloride solution and saturated aqueous solution of sodium chloride in that order, followed by drying over anhydrous sodium sulfate and then concentration under reduced pressure, to yield a crude product. The crude product was separated by column chromatography (petroleum ether/ethyl acetate=4:1) to yield Compound 1-2 as a pale brown solid (0.82 g, 59% yield). LRMS for $C_{14}H_{15}Cl_3N_3O$ $(M+H)^+$ m/z=346.0, MW=346.6360, in agreement with the calculated value from ChemDraw: Exact mass=345.0202.

3) Synthesis of 6-(4-amino-2,6-dichlorophenoxy)-4-(tert-butyl)pyridazin-3(2H)-one (1-3)

The compound 1-2 (0.82 g, 3.26 mmol) obtained in (2) above and sodium acetate (1.07 g, 13.04 mmol) were added into a 100 mL round-bottom flask and reacted in glacial acetic acid (20 mL) as a solvent at 120° C. for 24 h. LCMS indicated that the reaction was complete, and the reaction was stopped. The solvent was removed by rotary evaporation, and the residue was dissolved in water (10 mL), followed by the adjustment of pH value to pH 9-10 by using 1N HCl. The aqueous phase was extracted with ethyl acetate (25 mL×3), and the organic phases were then combined, washed with saturated sodium chloride solution, dried over anhydrous sodium sulfate and concentrated under reduced pressure to yield a crude product, which was used in the next reaction without further purification.

The obtained crude product was dissolved in methanol (20 mL), and 1N NaOH solution (20 mL) was added thereto. The mixture was reacted at 120° C. for 24 h. LCMS indicated that the reaction was complete, and the reaction was stopped. The solvent (i.e., methanol) was removed by rotary evaporation, and the residue (which was obtained as a suspension) was extracted with ethyl acetate (25 mL×3). The organic phases were combined, washed with saturated sodium chloride solution, dried over anhydrous sodium sulfate and concentrated under reduced pressure to yield a crude product. The crude product was separated by column chromatography (petroleum ether/ethyl acetate=2:1) to yield Compound 1-3 as a white solid (0.34 g, 44% yield). LRMS for $C_{14}H_{16}Cl_2N_3O_2$ (M+H)+ m/z=328.0, in agreement with the calculated value from ChemDraw: MW=328.1930, Exact mass=327.0541.

4) Synthesis of ethyl (Z)-(2-(2-(4-((5-(tert-butyl)-6-oxo-1,6-dihydropyridazin-3-yl)oxy)-3,5-dichlorophenyl)hydrazineylidene)-2-cyanoacetyl)carbamate (1-4)

The compound 1-3 (98 mg, 0.3 mmol) obtained in (3) above, concentrated hydrochloric acid (64 μL, 0.22 N), and glacial acetic acid (0.66 mL) were added into a 25 mL egg-plant type flask. After the mixture was stirred in an ice bath for 10 min, an aqueous solution of sodium nitrite (prepared by dissolving 21 mg (0.303 mmol) of $NaNO_2$ in 1 mL of water) was added dropwise thereto. When the mixture turned into a clear solution with constant stirring, an aqueous solution (1 mL) containing ethyl(2-cyanoacety)carbamate (47 mg, 0.303 mmol) and sodium acetate (68 mg, 0.825 mmol) was added dropwise thereto. The mixture was then transferred to a low-temperature reactor and stirred further 10 min to obtain an orange-red suspension. LCMS indicated that the reaction was complete, and the reaction was stopped. The suspension was subjected to suction filtration by a glass-fritted funnel. The filter cake was rinsed with water and then ethyl ether to yield an orange-red solid. The solid was dried in an oven at 50° C. for 4 h to yield Compound 1-4 as an orange-red solid (102 mg, 69% yield). LRMS for $C_{20}H_{21}Cl_2N_6O_5$ (M+H)+ m/z=495.1, in agreement with the calculated value from ChemDraw: MW=495.3170, Exact mass=494.0872.

5) Synthesis of 2-(4-((5-(tert-butyl)-6-oxo-1,6-dihydropyridazin-3-yl)oxy)-3,5-dichlorophenyl)-3,5-dioxo-2,3,4,5-tetrahydro-1,2,4-triazine-6-carbonitrile (1)

The compound 1-4 (102 mg, 0.21 mmol) obtained in (4) above was placed in a 10 mL microwave-transparent reaction tube, and potassium acetate (42 mg, 0.423 mmol) and DMF (3 mL) were added thereto. The reaction tube containing the mixture was then placed in microwave reactor to conduct a reaction at 140° C. for 30 min. LCMS indicated that the reaction was complete, and the reaction was stopped. The reaction mixture was diluted with ethyl acetate (20 mL), transferred into a 150 mL separatory funnel, and washed with water (10 mL). The organic phase was collected, washed with saturated sodium chloride solution, and dried over anhydrous sodium sulfate. The solvent was removed by rotary evaporation to yield a crude product. The crude product was separated by column chromatography (dichloromethane/methanol=30:1 to 10:1) to yield Compound 1 as a pale yellow solid (50 mg, 53% yield). HRMS m/z (ESI) calcd for $C_{18}H_{15}Cl_2N_6O_4$ (M+H)+ 449.0532, found 449.0530, in agreement with the calculated value from ChemDraw: MW=449.0525, Exact mass=448.0454; $^1H$ NMR (600 MHz, DMSO-$d_6$) δ 13.27 (s, 1H), 12.15 (s, 1H), 7.79 (s, 2H), 7.35 (s, 1H), 1.35 (s, 9H); $^{13}C$ NMR (150 MHz, DMSO-$d_6$) δ 170.8, 159.8, 155.2, 151.6, 147.7, 145.7, 137.9, 128.8 (2C), 127.1 (2C), 123.3, 120.1, 112.7, 27.9, 14.7 (3C).

Example 2 Synthesis of 2-(4-((5-(tert-butyl)-6-oxo-1,6-dihydropyridazin-3-yl)oxy)-3-fluorophenyl)-3,5-dioxo-2,3,4,5-tetrahydro-1,2,4-triazine-6-carbonitrile (2)

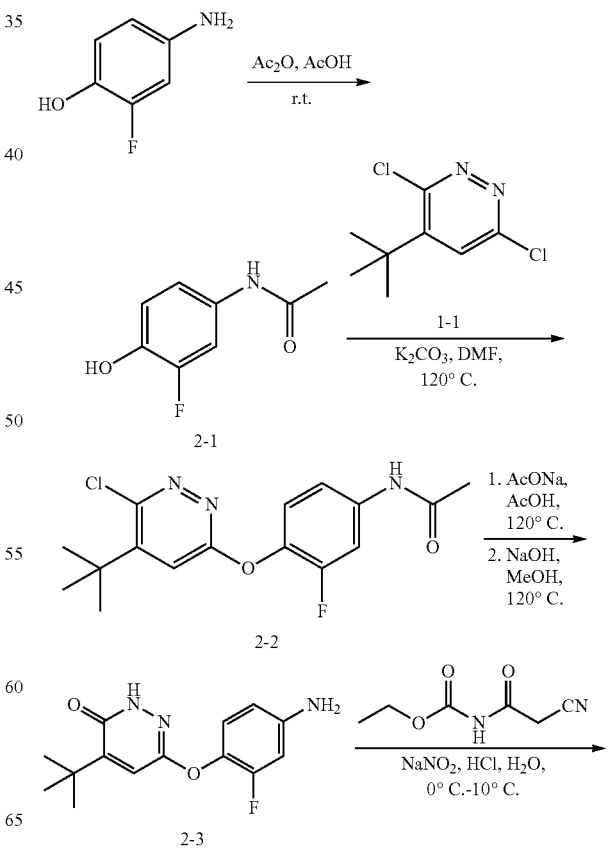

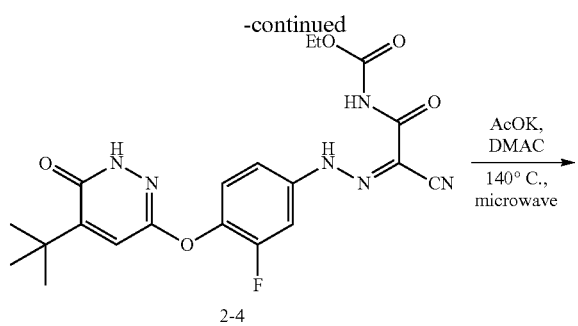

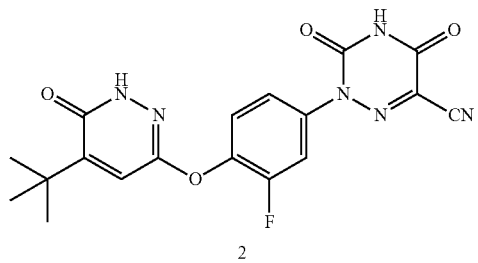

1) Synthesis of N-(3-fluoro-4-hydroxyphenyl)acetamide (2-1)

4-amino-2-fluorophenol (5.08 g, 40 mmol), acetic anhydride (4.08 g, 40 mmol), and glacial acetic acid (30 mL) were added into a 100 mL round-bottom flask and stirred overnight at room temperature. The solvent was removed by rotary evaporation. The residue (which was obtained as a solid) was rinsed several times with ethyl acetate and then dried in an oven at 50° C. for 4 h to yield Compound 2-1 as a brown solid (6.1 g, 90% yield). LRMS for $C_8H_9FNO_2$ $(M+H)^+$ m/z=170.1, in agreement with the calculated value from ChemDraw: MW=169.1554, Exact mass=169.0539.

2) Synthesis of N-(4-((5-(tert-butyl)-6-chloro-pyridazin-3-yl)oxy)-3-fluorophenyl)acetamide (2-2)

The compound 2-1 (0.62 g, 3.0 mmol) obtained in (1) above, 2,6-dichloro-4-aminophenol (0.51 g, 3.0 mmol), and potassium carbonate (0.83 g, 6.0 mmol) were added into a 100 mL round-bottom flask and reacted in DMF (10 mL) as a solvent at 120° C. for 3 h. TLC indicated that the reaction was complete, and the reaction was stopped. Then, after being cooled to room temperature, the reaction mixture was subjected to suction filtration by Celite which had been loaded into a glass-fritted funnel. The filter cake was rinsed with several sequential rinses of ethyl acetate. The filtrate and rinse were combined and washed with 10% aqueous sodium chloride solution and saturated aqueous solution of sodium chloride in that order, followed by drying over anhydrous sodium sulfate and then concentration under reduced pressure, to yield a crude product. The crude product was separated by column chromatography (petroleum ether/ethyl acetate=4:1) to yield Compound 2-2 as a brown solid (0.8 g, 82% yield). LRMS for $C_{16}H_{18}ClFN_3O_2$ $(M+H)^+$ m/z=338.1, in agreement with the calculated value from ChemDraw: MW=337.7794, Exact mass=337.0993.

3) Synthesis of 6-(4-amino-2-fluorophenoxy)-4-(tert-butyl)pyridazin-3(2H)-one (2-3)

The compound 2-2 (0.8 g, 2.37 mmol) obtained in (2) above and sodium acetate (0.78 g, 9.48 mmol) were added into a 100 mL round-bottom flask and reacted in glacial acetic acid (20 mL) as a solvent at 120° C. for 24 h. LCMS indicated that the reaction was complete, and the reaction was stopped. The solvent was removed by rotary evaporation, and the residue was dissolved in water (10 mL), followed by the adjustment of pH value to pH 9-10 by using 1N HCl. The aqueous phase was extracted with ethyl acetate (25 mL×3), and the organic phases were then combined, washed with saturated sodium chloride solution, dried over anhydrous sodium sulfate and concentrated under reduced pressure to yield a crude product, which was used in the next reaction without further purification.

The obtained crude product was dissolved in methanol (15 mL), and 1N NaOH solution (15 mL) was added thereto. The mixture was reacted at 120° C. for 24 h. LCMS indicated that the reaction was complete, and the reaction was stopped. The solvent (i.e., methanol) was removed by rotary evaporation, and the residue (which was obtained as a suspension) was extracted with ethyl acetate (25 mL×3). The organic phases were combined, washed with saturated sodium chloride solution, dried over anhydrous sodium sulfate and concentrated under reduced pressure to yield a crude product. The crude product was separated by column chromatography (petroleum ether/ethyl acetate=2:1) to yield Compound 2-3 as a white solid (0.40 g, 62% yield). LRMS for $C_{14}H_{17}FN_3O_2$ $(M+H)^+$ m/z=278.1, in agreement with the calculated value from ChemDraw: MW=277.2994, Exact mass=277.1227.

4) Synthesis of ethyl (Z)-(2-(2-(4-((5-(tert-butyl)-6-oxo-1,6-dihydropyridazin-3-yl)oxy)-3-fluorophenyl)hydrazine ylidene)-2-cyanoacetyl)carbamate (2-4)

The compound 2-3 (98 mg, 0.3 mmol) obtained in (3) above, concentrated hydrochloric acid (64 μL, 0.22 N), and glacial acetic acid (0.66 mL) were added into a 25 mL egg-plant type flask. After the mixture was stirred in an ice bath for 10 min, an aqueous solution of sodium nitrite (prepared by dissolving 21 mg (0.303 mmol) of $NaNO_2$ in 1 mL of water) was added dropwise thereto. When the mixture turned into a clear solution with constant stirring, an aqueous solution (1 mL) containing ethyl(2-cyanoacety)carbamate (47 mg, 0.303 mmol) and sodium acetate (68 mg, 0.825 mmol) was added dropwise thereto. The mixture was then transferred to a low-temperature reactor and stirred further 10 min at 10° C. to obtain an orange-red suspension. LCMS indicated that the reaction was complete, and the reaction was stopped. The suspension was subjected to suction filtration by a glass-fritted funnel. The filter cake was rinsed with water and then ethyl ether to yield an orange-red solid. The solid was dried in an oven at 50° C. for 4 h to yield Compound 2-4 as an orange-red solid (100 mg, 75% yield). LRMS for $C_{20}H_{22}FN_6O_5$ $(M+H)^+$ m/z=445.1, in agreement with the calculated value from ChemDraw: MW=444.4234, Exact mass=444.1557.

5) Synthesis of 2-(4-((5-(tert-butyl)-6-oxo-1,6-dihydropyridazin-3-yl)oxy)-3-fluorophenyl)-3,5-dioxo-2,3,4,5-tetrahydro-1,2,4-triazine-6-carbonitrile (2)

The compound 2-4 (100 mg, 0.23 mmol) obtained in (4) above was placed in a 10 mL microwave-transparent reaction tube, and potassium acetate (45 mg, 0.46 mmol) and DMF (3 mL) were added thereto. The reaction tube containing the mixture was then placed in microwave reactor to conduct a reaction at 140° C. for 30 min. LCMS indicated that the reaction was complete, and the reaction was stopped. The reaction mixture was diluted with ethyl acetate (20 mL), transferred into a 150 mL separatory funnel, and washed with water (10 mL). The organic phase was collected, washed with saturated sodium chloride solution, and dried over anhydrous sodium sulfate. The solvent was removed by rotary evaporation to yield a crude product. The crude product was separated by column chromatography (dichloromethane/methanol=30:1 to 10:1) to yield Compound 2 as a pale yellow solid (56 mg, 61% yield). HRMS m/z (ESI) calcd for $C_{18}H_{16}FN_6O_4$ (M+H)$^+$ 399.1217, found 399.1214, in agreement with the calculated value from ChemDraw: MW=398.3544, Exact mass=398.1139; $^1$H NMR (600 MHz, DMSO-d$_6$) δ 12.12 (s, 1H), 7.57 (dd, J=11.4, 2.4 Hz, 1H), 7.51-7.48 (m, 1H), 7.41-7.35 (m, 1H), 7.25 (s, 1H), 1.34 (s, 9H); $^{13}$C NMR (150 MHz, DMSO-d$_6$) δ 159.8, 159.0, 154.4, 153.4 (J=246 Hz), 152.8, 150.5, 139.7 (J=12 Hz), 138.8 (J=10.5 Hz), 124.1, 122.9 (J=3 Hz), 122.8, 120.8, 115.1 (J=21 Hz), 114.2, 35.8, 27.8 (3C).

Example 3 Synthesis of 1-(3,5-dichloro-4-((5-cyclobutyl-6-oxo-1,6-dihydropyridazin-3-yl)oxy)phenyl)-2,4-dioxo-1,2,3,4-tetrahydropyrimidine-5-carbonitrile (42)

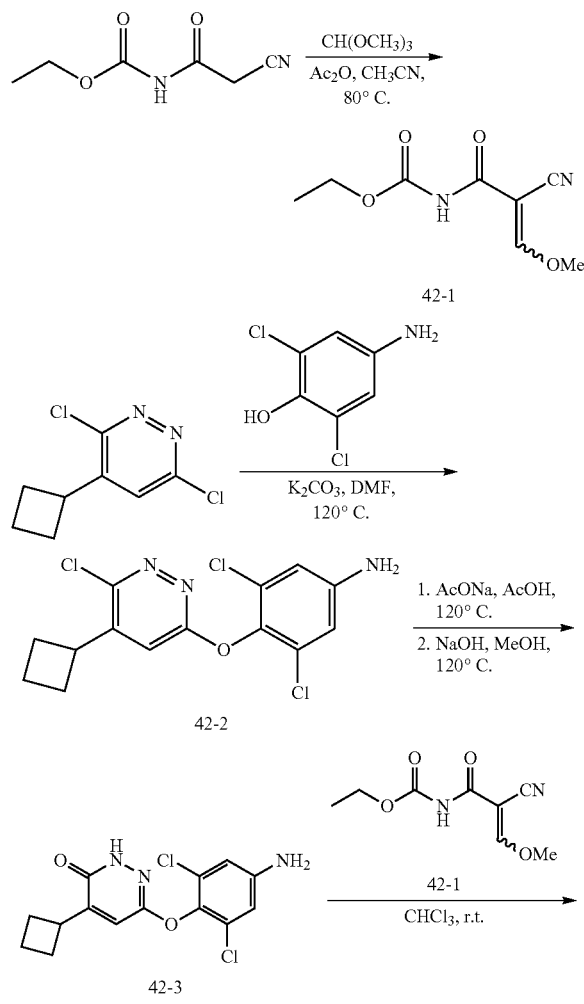

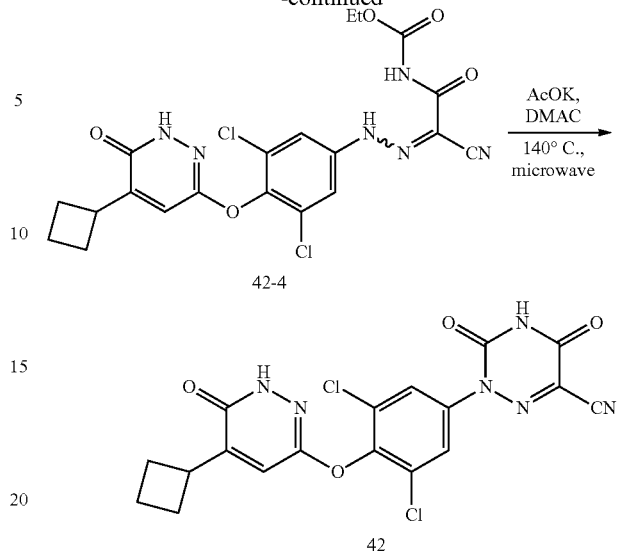

1) Synthesis of ethyl (2-cyano-3-methoxyacryloyl)carbamate (42-1)

Ethyl carbamate (3.12 g, 20 mmol) and 40 mL of acetonitrile were added into a 100 mL egg-plant type flask and the mixture was stirred until complete dissolution was achieved. Trimethyl orthoformate (TMOF, 3.5 mL, 40 mmol) and acetic anhydride (20 mL) were then added thereto. The resulting mixture was heated to 80° C., and reacted for 4 h. Then, the reaction was stopped. The solvent was removed by rotary evaporation to leave a residue, to which 50 mL of ethyl ether was added to give a suspension. The suspension was allowed to stand overnight in a refrigerator at 2 to 8° C. and was then filtered. The filter cake was rinsed several times with ethyl ether and was then dried in an oven at 50° C. for 4 h to yield Compound 42-1 as a white solid (2.2 g, 56% yield). LRMS for $C_8H_{11}N_2O_4$ (M+H)$^+$ m/z=199.1, in agreement with the calculated value from ChemDraw: MW=198.1780, Exact mass=198.0641.

2) Synthesis of 3,5-dichloro-4-((6-chloro-5-cyclobutylpyridazin-3-yl)oxy)aniline (42-2)

3,6-dichloro-4-cyclobutylpyridine (1.62 g, 8.0 mmol), 2,6-dichloro-4-aminophenol (1.42 g, 8.0 mmol), and potassium carbonate (2.21 g, 16.0 mmol) were added into a 100 mL round-bottom flask and reacted in DMF (20 mL) as a solvent at 120° C. for 3 h. TLC indicated that the reaction was complete, and the reaction was stopped. Then, after being cooled to room temperature, the reaction mixture was subjected to suction filtration by Celite which had been loaded into a glass-fritted funnel. The filter cake was rinsed with several sequential rinses of ethyl acetate. The filtrate and rinse were combined and washed with 10% aqueous sodium chloride solution and saturated aqueous solution of sodium chloride in that order, followed by drying over anhydrous sodium sulfate and then concentration under reduced pressure, to yield a crude product. The crude product was separated by column chromatography (petroleum ether/ethyl acetate=4:1) to yield Compound 42-2 as a pale brown solid (1.36 g, 50% yield). LRMS for $C_{14}H_{13}Cl_3N_3O$ (M+H)$^+$ m/z=344.0, in agreement with the calculated value from ChemDraw: MW=344.6200, Exact mass=343.0046.

3) Synthesis of 6-(4-amino-2,6-dichlorophenoxy)-4-cyclobutylpyridazin-3(2H)-one (42-3)

The compound 42-2 (1.36 g, 3.97 mmol) obtained in (2) above and sodium acetate (1.3 g, 15.86 mmol) were added into a 100 mL round-bottom flask and reacted in glacial acetic acid (20 mL) as a solvent at 120° C. for 24 h. LCMS indicated that the reaction was complete, and the reaction was stopped. The solvent was removed by rotary evaporation, and the residue was dissolved in water (10 mL), followed by the adjustment of pH value to pH 9-10 by using 1N HCl. The aqueous phase was extracted with ethyl acetate (25 mL×3), and the organic phases were then combined, washed with saturated sodium chloride solution, dried over anhydrous sodium sulfate and concentrated under reduced pressure to yield a crude product, which was used in the next reaction without further purification.

The obtained crude product was dissolved in methanol (24 mL), and 1N NaOH solution (24 mL) was added thereto. The mixture was reacted at 120° C. for 24 h. LCMS indicated that the reaction was complete, and the reaction was stopped. The solvent (i.e., methanol) was removed by rotary evaporation, and the residue (which was obtained as a suspension) was extracted with ethyl acetate (25 mL×3). The organic phases were combined, washed with saturated sodium chloride solution, dried over anhydrous sodium sulfate and concentrated under reduced pressure to yield a crude product. The crude product was separated by column chromatography (petroleum ether/ethyl acetate=2:1) to yield Compound 42-3 as a gray solid (0.57 g, 44% yield). LRMS for $C_{14}H_{14}Cl_2N_3O_2$ (M+H)$^+$ m/z=326.0, in agreement with the calculated value from ChemDraw: MW=326.1770, Exact mass=325.0385.

4) Synthesis of ethyl (2-cyano-3-((3,5-dichloro-4-((5-cyclobutyl-6-oxo-1,6-dihydropyridazin-3-yl)oxy)phenyl)amino)acryloyl)carbamate (42-4)

The compounds 42-1 (71 mg, 0.36 mmol) and 42-3 (98 mg, 0.3 mmol) obtained in (1) and (3) above, respectively, and 5 mL of chloroform were added into a 10 mL egg-plant type flask. The mixture was refluxed for 1 h to complete the reaction. After being cooled to room temperature, the reaction mixture (which was obtained as a suspension) was filtered and the filter cake was rinsed with ethyl ether and then dried at 50° C. to yield Compound 42-4 as a white solid (80 mg, 54% yield). LRMS for $C_{21}H_{20}Cl_2N_2O_5$ (M+H)$^+$ m/z=492.1, in agreement with the calculated value from ChemDraw: MW=492.2130, Exact mass=491.0763.

5) Synthesis of 1-(3,5-dichloro-4-((5-cyclobutyl-6-oxo-1,6-dihydropyridazin-3-yl)oxy)phenyl)-2,4-dioxo-1,2,3,4-tetrahydropyrimidine-5-carbonitrile (42)

The compound 42-4 (80 mg, 0.17 mmol) obtained in (4) above was placed in a 10 mL microwave-transparent reaction tube, and potassium acetate (33 mg, 0.34 mmol) and DMF (2 mL) were added thereto. The reaction tube containing the mixture was then placed in microwave reactor to conduct a reaction at 140° C. for 30 min. LCMS indicated that the reaction was complete, and the reaction was stopped. The reaction mixture was diluted with ethyl acetate (20 mL), transferred into a 150 mL separatory funnel, and washed with water (10 mL). The organic phase was collected, washed with saturated sodium chloride solution, and dried over anhydrous sodium sulfate. The solvent was removed by rotary evaporation to yield a crude product. The crude product was separated by column chromatography (dichloromethane/methanol=30:1 to 10:1) to yield Compound 42 as a pale yellow solid (37 mg, 52% yield). HRMS m/z (ESI) calcd for $C_{19}H_{14}Cl_2N_5O_4$ (M+H)$^+$ 446.0423, found 446.0420, in agreement with the calculated value from ChemDraw: MW=446.2440, Exact mass=445.0345; $^1$H NMR (600 MHz, DMSO-d$_6$) δ 12.31 (s, 1H), 12.22 (s, 1H), 8.90 (s, 1H), 7.88 (s, 2H), 7.50 (s, 1H), 3.59-3.53 (m, 1H), 2.30-2.24 (m, 2H), 2.19-2.10 (m, 2H), 2.07-1.97 (m, 1H), 1.85-1.80 (m, 1H); $^{13}$C NMR (150 MHz, DMSO-d$_6$) δ 160.9, 160.0, 154.7, 151.5, 151.4, 149.5, 145.9, 136.4, 128.9 (2C), 128.7 (2C), 120.0, 114.4, 89.2, 35.5, 27.3 (2C), 18.3.

Example 4 Synthesis of 6-(2,6-dichloro-4-(5-hydroxy-6-oxo-1,6-dihydropyridin-3-yl)phenoxy)-4-isopropylpyridazin-3(2H)-one (47)

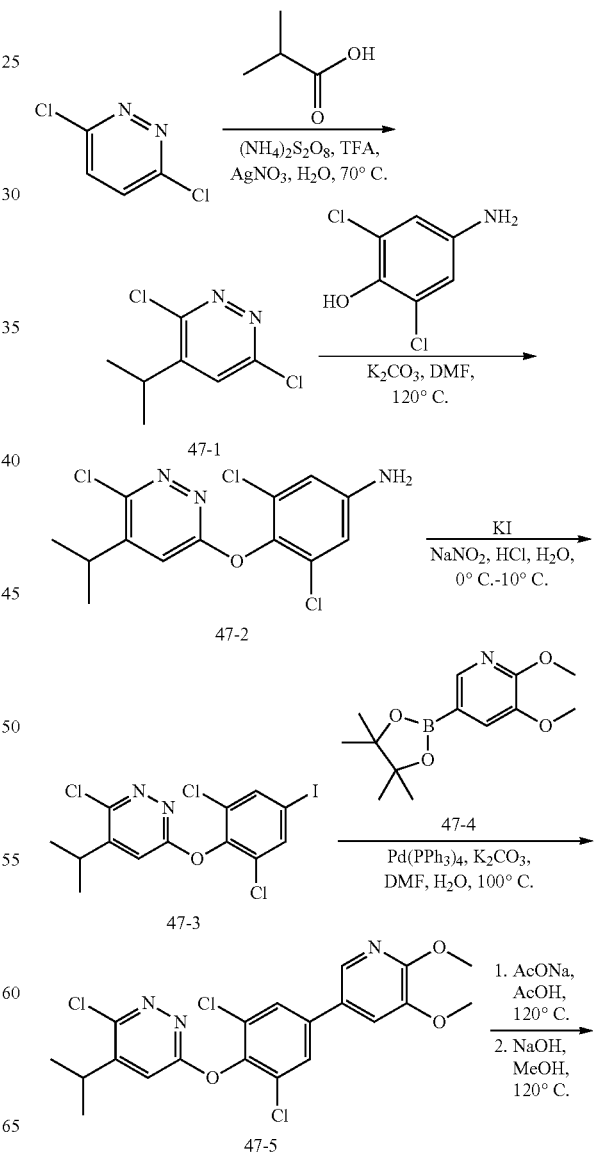

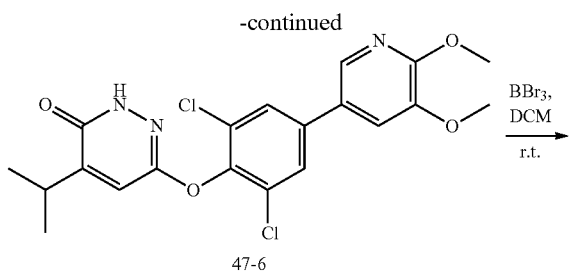

1) Synthesis of 3,6-dichloro-4-isopropylpyridazine (47-1)

To a 1 L round-bottom flask were added 3,6-dichloropyridazine (14.9 g, 0.1 mol), isobutyric acid (17.6 g, 0.2 mol), purified water (300 mL), and TFA (7.4 mL, 0.1 mol). When the mixture was heated to 70° C., silver nitrate (3.4 g, 0.2 mol) was added thereto. Then, to the resulting mixture was added an aqueous ammonium persulfate solution (prepared by dissolving 91.3 g of solid ammonium persulfate in 200 mL of water) to conduct a reaction at 70° C. for 30 min. TLC indicated that the reaction was complete, and the reaction was stopped. Then, after the reaction mixture was allowed to cool to room temperature, concentrated aqueous ammonia was added to adjust a pH to pH 9-10, followed by extraction with ethyl acetate (200 mL×3). The organic phases were combined, washed with saturated sodium chloride solution, dried over anhydrous sodium sulfate and concentrated under reduced pressure to yield a crude product. The crude product was separated by column chromatography (petroleum ether/ethyl acetate=20:1) to yield Compound 47-1 as a colorless liquid (8.93 g, 47% yield). LRMS for $C_7H_9Cl_2N_2$ $(M+H)^+$ m/z=191.0, in agreement with the calculated value from ChemDraw: MW=191.0550, Exact mass=190.0065.

2) Synthesis of 3,5-dichloro-4-((6-chloro-5-isopropylpyridazin-3-yl)oxy)aniline (47-2)

The compound 47-1 (1.52 g, 8.0 mmol) obtained in (1) above, 2,6-dichloro-4-aminophenol (1.42 g, 8.0 mmol), and potassium carbonate (2.20 g, 16.0 mmol) were added into a 100 mL round-bottom flask and reacted in DMF (20 mL) as a solvent at 120° C. for 3 h. TLC indicated that the reaction was complete, and the reaction was stopped. Then, the reaction mixture was allowed to cool to room temperature and was then subjected to suction filtration by Celite which had been loaded into a glass-fritted funnel. The filter cake was rinsed with several sequential rinses of ethyl acetate. The filtrate and rinse were combined and washed with 10% aqueous sodium chloride solution and saturated aqueous solution of sodium chloride in that order, followed by drying over anhydrous sodium sulfate and then concentration under reduced pressure, to yield a crude product. The crude product was separated by column chromatography (petroleum ether/ethyl acetate=4:1) to yield Compound 47-2 as a pale brown solid (1.62 g, 61% yield). LRMS for $C_{13}H_{13}Cl_3N_3O$ $(M+H)^+$ m/z=332.0, in agreement with the calculated value from ChemDraw: MW=332.6090, Exact mass=331.0046.

3) Synthesis of 3-chloro-6-(2,6-dichloro-4-iodophenoxy)-4-isopropylpyridazine (47-3)

The compound 47-2 (0.99 g, 3 mmol) obtained in (2) above, concentrated hydrochloric acid (0.64 mL, 0.22 N), and glacial acetic acid (6.6 mL) were added into a 25 mL egg-plant type flask. After the mixture was stirred in an ice bath for 10 min, an aqueous solution of sodium nitrite (prepared by dissolving 210 mg (3.03 mmol) of $NaNO_2$ in 10 mL of water) was added dropwise thereto. When the mixture turned into a clear solution with constant stirring, an aqueous solution (10 mL) containing potassium iodide (503 mg, 3.03 mmol) and sodium acetate (680 mg, 8.25 mmol) was added dropwise thereto. The mixture was then transferred to a low-temperature reactor and stirred further 30 min at 10° C. to obtain a brown suspension. LCMS indicated that the reaction was complete, and the reaction was stopped. The suspension was subjected to suction filtration by a glass-fritted funnel. The filter cake was rinsed with water and then ethyl ether to yield an orange-red solid. The solid was dried in an oven at 50° C. for 4 h to yield Compound 47-3 as a brown solid (862 mg, 65% yield). LRMS for $C_{13}H_{11}Cl_3N_2O$ $(M+H)^+$ m/z=442.9, in agreement with the calculated value from ChemDraw: MW=443.4905, Exact mass=441.8903.

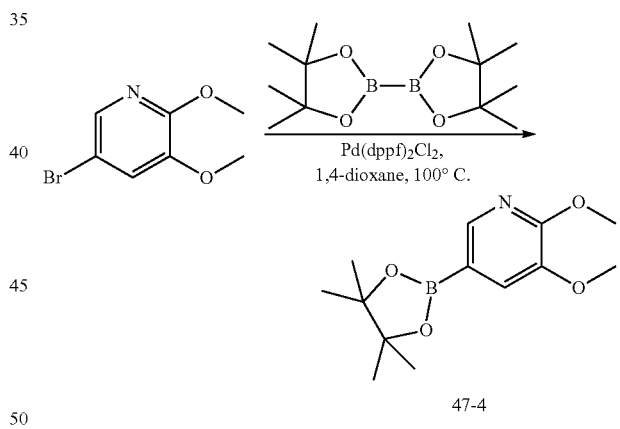

47-4

Synthesis of 2,3-dimethoxy-5-(4,4,5,5-tetramethyl-1,3,2-dioxaborolan-2-yl)pyridine (47-4)

4) Synthesis of 2,3-dimethoxy-5-(4,4,5,5-tetramethyl-1,3,2-dioxaborolan-2-yl)pyridine (47-4)

A magnetic stirrer was put into a 100 mL two neck flask. One neck was equipped with a rubber cork and the other was equipped with a three-way cock. The flask was evacuated and flushed with nitrogen. The evacuation and breaking of the vacuum with nitrogen were repeated three times. Then, to the flask were successively added 5-bromo-2,3-dimethoxypyridine (2.17 g, 10 mmol), bis(pinacolato)diboron (2.54 g, 10 mmol), [1,1'-bis(diphenylphosphino)ferrocene]dichloropalladium(II) (732 mg, 1 mmol), and anhydrous 1,4-dioxane (50 mL) under nitrogen. The mixture was reacted at 100° C. for 3 h. LCMS indicated that the reaction was complete, and the reaction was stopped. The reaction mixture was concentrated under reduced pressure to yield a crude product, which was separated by column chromatography (petroleum ether/ethyl acetate=10:1) to yield Compound 47-4 as a pale yellow solid (2.2 g, 83% yield). LRMS for $C_{13}H_{21}BNO_4$ (M+H)$^+$ m/z=266.1, in agreement with the calculated value from ChemDraw: MW=265.1160, Exact mass=265.1485.

5) Synthesis of 3-chloro-6-(2,6-dichloro-4-(5,6-dimethoxypyridin-3-yl)phenoxy)-4-isopropylpyridazine (47-5)

A magnetic stirrer was put into a 25 mL two neck flask. One neck was equipped with a rubber cork and the other was equipped with a three-way cock. The flask was evacuated and flushed with nitrogen. The evacuation and breaking of the vacuum with nitrogen were repeated three times. Then, to the flask were successively added the compound 47-4 (0.53 g, 2 mmol) obtained in (4) above, the compound 47-3 (0.88 g, 2 mmol) obtained in (3) above, tetrakis(triphenylphosphine)palladium (46 mg, 0.04 mmol), potassium carbonate (0.55 g, 4 mmol), and a mixed solvent of DMF and water (DMF/$H_2O$=4:1, 10 mL) under nitrogen. The mixture was reacted at 110° C. for 3 h. LCMS indicated that the reaction was complete, and the reaction was stopped. The reaction mixture was concentrated under reduced pressure to yield a crude product, which was separated by column chromatography (petroleum ether/ethyl acetate=4:1) to yield Compound 47-5 as a pale brown solid (643 mg, 71% yield). LRMS for $C_{20}H_{19}Cl_3N_3O_3$ (M+H)$^+$ m/z=454.0, in agreement with the calculated value from ChemDraw: MW=454.7320, Exact mass=453.0414.

6) Synthesis of 6-(2,6-dichloro-4-(5,6-dimethoxypyridin-3-yl)phenoxy)-4-isopropylpyridazin-3(2H)-one (47-6)

The compound 47-5 (0.45 g, 1 mmol) obtained in (5) above and sodium acetate (1.32 g, 4 mmol) were added into a 100 mL round-bottom flask and reacted in glacial acetic acid (10 mL) as a solvent at 120° C. for 24 h. LCMS indicated that the reaction was complete, and the reaction was stopped. The solvent was removed by rotary evaporation, and the residue was dissolved in water (10 mL), followed by the adjustment of pH value to pH 9-10 by using 1N HCl. The aqueous phase was extracted with ethyl acetate (25 mL×3), and the organic phases were then combined, washed with saturated sodium chloride solution, dried over anhydrous sodium sulfate and concentrated under reduced pressure to yield a crude product, which was used in the next reaction without further purification.

The obtained crude product was dissolved in methanol (6 mL), and 1N NaOH solution (6 mL) was added thereto. The mixture was reacted at 120° C. for 24 h. LCMS indicated that the reaction was complete, and the reaction was stopped. The solvent (i.e., methanol) was removed by rotary evaporation, and the residue (which was obtained as a suspension) was extracted with ethyl acetate (25 mL×3). The organic phases were combined, washed with saturated sodium chloride solution, dried over anhydrous sodium sulfate and concentrated under reduced pressure to yield a crude product. The crude product was separated by column chromatography (petroleum ether/ethyl acetate=1:1) to yield Compound 47-6 as a pale brown solid (221 mg, 51% yield). LRMS for $C_{20}H_{20}Cl_2N_2O_4$ (M+m/z=436.1, in agreement with the calculated value from ChemDraw: MW=436.2890, Exact mass=435.0753.

7) Synthesis of 6-(2,6-dichloro-4-(5-hydroxy-6-oxo-1,6-dihydropyridin-3-yl)phenoxy)-4-isopropylpyridazin-3(2H)-one (47)

The compound 47-6 (221 mg, 0.51 mmol) obtained in (6) above was dissolved in 5 mL of dichloromethane, and boron tribromide solution (2 mL, 1N solution in dichloromethane) was added thereto. The mixture was stirred and reacted at room temperature for 20 h. TLC indicated that the reaction was complete, and the reaction was stopped. The solvent was removed by rotary evaporation to leave a residue, to which hydrochloric acid solution (2 mL, 3N) was added to give a suspension. The suspension was then filtered to yield a white solid, which was dissolved in dichloromethane, and washed with saturated sodium bicarbonate solution and then saturated sodium chloride solution. The organic phases were combined, dried over anhydrous sodium sulfate and concentrated under reduced pressure to yield a crude product. The crude product was separated by column chromatography (dichloromethane/methanol=150:1) to yield Compound 47 as a pale yellow solid (128 mg, 62% yield). HRMS m/z (ESI) calcd for $C_{18}H_{16}Cl_2N_3O_4$ (M+H)$^+$ 408.0518, found 408.0515, in agreement with the calculated value from ChemDraw: MW=408.2350, Exact=407.0440; $^1$H NMR (600 MHz, DMSO-$d_6$) δ 13.22 (s, 1H), 11.24 (s, 1H), 10.69 (s, 1H), 8.05 (s, 1H), 7.92 (s, 2H), 7.65 (s, 1H), 7.43 (s, 1H), 3.05 (hept, J=7.2 Hz, 1H), 1.20 (d, J=7.2 Hz, 6H); $^{13}$C NMR (150 MHz, DMSO-$d_6$) δ 176.5, 163.0, 162.6, 151.4, 151.0, 150.3, 127.9, 125.9 (2C), 125.5 (2C), 123.6, 123.5, 122.7, 118.0, 28.2, 21.0 (2C).

Example 5 Synthesis of 6-(2,6-dichloro-4-(2H-tetrazol-5-yl)phenoxy)-4-isopropylpyridazin-3(2H)-one (49)

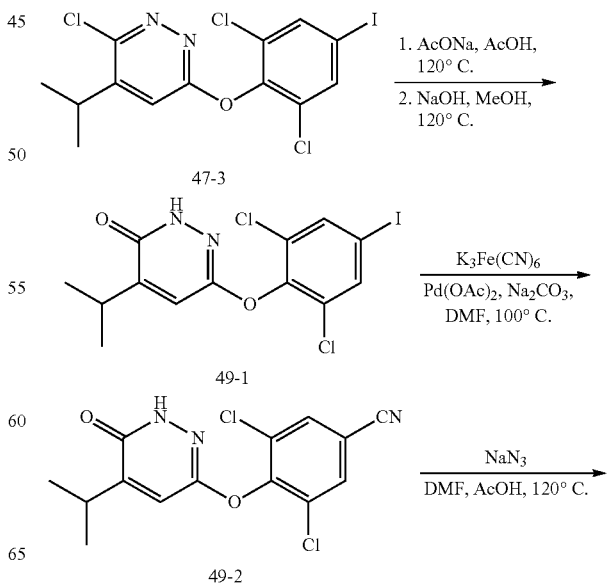

-continued

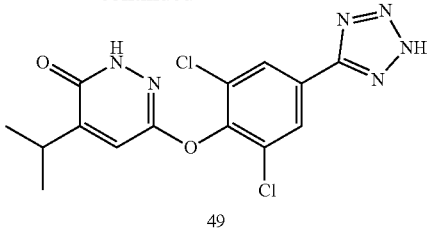

49

1) Synthesis of 6-(2,6-dichloro-4-iodophenoxy)-4-isopropylpyridazin-3(2H)-one (49-1)

The compound 47-3 (0.44 g, 1 mmol) obtained in (3) above in Example 4 and sodium acetate (1.32 g, 4 mmol) were added into a 100 mL round-bottom flask and reacted in glacial acetic acid (10 mL) as a solvent at 120° C. for 24 h. LCMS indicated that the reaction was complete, and the reaction was stopped. The solvent was removed by rotary evaporation, and the residue was dissolved in water (10 mL), followed by the adjustment of pH value to pH 9-10 by using 1N HCl. The aqueous phase was extracted with ethyl acetate (25 mL×3), and the organic phases were then combined, washed with saturated sodium chloride solution, dried over anhydrous sodium sulfate and concentrated under reduced pressure to yield a crude product, which was used in the next reaction without further purification.

The obtained crude product was dissolved in methanol (6 mL), and 1N NaOH solution (6 mL) was added thereto. The mixture was reacted at 120° C. for 24 h. LCMS indicated that the reaction was complete, and the reaction was stopped. The solvent (i.e., methanol) was removed by rotary evaporation, and the residue (which was obtained as a suspension) was extracted with ethyl acetate (25 mL×3). The organic phases were combined, washed with saturated sodium chloride solution, dried over anhydrous sodium sulfate and concentrated under reduced pressure to yield a crude product. The crude product was separated by column chromatography (petroleum ether/ethyl acetate=1:1) to yield Compound 49-1 as a pale brown solid (276 mg, 65% yield). LRMS for $C_{13}H_{12}Cl_2IN_2O_2$ $(M+H)^+$ m/z=425.0, in agreement with the calculated value from ChemDraw: MW=425.0475, Exact mass=423.9242.

2) Synthesis of 3,5-dichloro-4-((5-isopropyl-6-oxo-1,6-dihydropyridazin-3-yl)oxy)benzonitrile (49-2)

A magnetic stirrer was put into a 25 mL two neck flask. One neck was equipped with a rubber cork and the other was equipped with a three-way cock. The flask was evacuated and flushed with nitrogen. The evacuation and breaking of the vacuum with nitrogen were repeated three times. Then, to the flask were successively added the compound 49-1 (0.42 g, 1 mmol) obtained in (1) above, palladium acetate (23 mg, 0.01 mmol), potassium carbonate (0.28 g, 2 mmol), and DMF (10 mL) under nitrogen. The mixture was reacted at 110° C. for 2 h. LCMS indicated that the reaction was complete, and the reaction was stopped. The reaction mixture was concentrated under reduced pressure to yield a crude product, which was separated by column chromatography (petroleum ether/ethyl acetate=4:1) to yield Compound 49-2 as a pale yellow solid (256 mg, 80% yield). LRMS for $C_{14}H_{12}Cl_2N_3O_2$ $(M+H)^+$ m/z=324.0, in agreement with the calculated value from ChemDraw: MW=324.1610, Exact mass=323.0228.

3) Synthesis of 6-(2,6-dichloro-4-(2H-tetrazol-5-yl)phenoxy)-4-isopropylpyridazin-3(2H)-one (49)

To a 10 mL pressure tube were added the compound 49-2 (96 mg, 0.3 mmol) obtained in (2) above, sodium azide (78 mg, 1.2 mmol), DMF (4.0 mL), and glacial acetic acid (0.3 mL). The mixture was reacted at 120° C. for 4 h. TLC indicated that the reaction was complete, and the reaction was stopped. The solvent was removed by rotary evaporation to leave a residue, to which a 3N hydrochloric acid solution (2 mL) was added to yield a suspension. The suspension was extracted with ethyl acetate (10 mL×3). The organic phases were combined, washed with saturated sodium chloride solution, dried over anhydrous sodium sulfate and concentrated under reduced pressure to yield a crude product. The crude product was separated by column chromatography (dichloromethane/methanol=10:1) to yield Compound 49 as a pale yellow solid (74 mg, 67% yield). HRMS m/z (ESI) calcd for $C_{14}H_{13}Cl_2N_6O_2$ $(M+H)^+$ 367.0477, found 367.0475, in agreement with the calculated value from ChemDraw: MW=367.1900, Exact mass=366.0399; $^1H$ NMR (600 MHz, DMSO-$d_6$) δ 13.22 (s, 1H), 11.24 (s, 1H), 10.69 (s, 1H), 8.05 (s, 1H), 7.92 (s, 2H), 7.65 (s, 1H), 7.43 (s, 1H), 3.05 (hept, J=7.2 Hz, 1H), 1.20 (d, J=7.2 Hz, 6H); $^{13}C$ NMR (150 MHz, DMSO-$d_6$) 176.5, 163.0, 162.6, 151.4, 151.0, 150.3, 127.9, 125.9 (2C), 125.5 (2C), 123.6, 123.5, 122.7, 118.0, 28.2, 21.0 (2C).

Compounds 1 to 50 except 1, 2, 42, 47, and 49 were prepared as follows.

Compound 3 was prepared from pivalic acid, 3,6-dichloropyridazine, and 2-chloro-4-aminophenol in a similar manner to that of Example 1. It was obtained as a pale yellow solid. HRMS m/z (ESI) calcd for $C_{18}H_{16}ClN_6O_4$ $(M+H)^+$ 415.0922, found 415.0916, in agreement with the calculated value from ChemDraw: MW=414.8060, Exact mass=414.0843; $^1H$ NMR (400 MHz, DMSO-$d_6$) δ 12.13 (s, 1H), 7.74 (s, 1H), 7.57-7.51 (m, 2H), 7.25 (s, 1H), 1.34 (s, 9H); $^{13}C$ NMR (150 MHz, DMSO-$d_6$) δ 159.8, 157.0, 154.5, 152.8, 149.1, 148.9, 138.1, 128.1, 126.6, 126.1, 124.3, 122.9, 120.9, 113.4, 35.8, 27.9 (3C).

Compound 4 was prepared from pivalic acid, 3,6-dichloropyridazine, and 3-chloro-4-aminophenol in a similar manner to that of Example 1. It was obtained as a gray solid. HRMS m/z (ESI) calcd for $C_{18}H_{16}ClN_6O_4$ $(M+H)^+$ 415.0922, found 415.0920, in agreement with the calculated value from ChemDraw: MW=414.8060, Exact mass=414.0843; $^1H$ NMR (600 MHz, DMSO-$d_6$) δ 12.17 (s, 1H), 7.58-7.55 (m, 2H), 7.30 (dd, J=9.0, 3.0 Hz, 1H), 7.18 (s, 1H), 1.33 (s, 9H); $^{13}C$ NMR (150 MHz, DMSO-$d_6$) δ 159.9, 157.2, 154.2, 154.2, 153.1, 136.0, 132.3, 131.2, 125.0, 122.7, 122.6, 121.7, 120.8, 114.8, 39.6, 27.9 (3C).

Compound 5 was prepared from pivalic acid, 3,6-dichloropyridazine, and 2-methoxy-4-aminophenol in a similar manner to that of Example 1. It was obtained as a pale yellow solid. HRMS m/z (ESI) calcd for $C_{19}H_{19}N_6O_5$ $(M+H)^+$ 411.1417, found 411.1412, in agreement with the calculated value from ChemDraw: MW=410.3900, Exact mass=410.1339; $^1H$ NMR (600 MHz, DMSO-$d_6$) δ 13.07 (s, 1H), 11.98 (s, 1H), 7.33 (d, J=8.4 Hz, 1H), 7.27 (d, J=1.8 Hz, 1H), 7.18 (s, 1H), 7.10 (dd, J=8.4, 1.8 Hz, 1H), 2.50 (s, 3H), 1.33 (s, 9H); $^{13}C$ NMR (150 MHz, DMSO-$d_6$) δ 159.8, 155.3, 153.9, 153.2, 151.6, 147.6, 142.0, 137.6, 123.4, 122.6, 121.0, 119.2, 112.9, 111.7, 56.6, 35.7, 27.9 (3C).

Compounds 6 and 13 were prepared from 2-cyclopentylacetic acid, 3,6-dichloropyridazine, and 2,6-dichloro-4-aminophenol in a similar manner to that of Example 1. The former was obtained as a pale yellow solid. HRMS m/z (ESI) calcd for $C_{20}H_{17}Cl_2N_6O_4$ (M+H)$^+$ 475.0688, found 475.0677, in agreement with the calculated value from ChemDraw: MW=474.0610, Exact mass=470.0338; $^1$H NMR (600 MHz, DMSO-d$_6$) δ 12.23 (s, 1H), 7.79 (s, 2H), 7.51 (s, 1H), 2.52 (d, J=7.2 Hz, 2H), 2.25-2.20 (m, 1H), 1.75-1.68 (m, 2H), 1.65-1.60 (m, 2H), 1.55-1.51 (m, 2H), 1.25-1.18 (m, 2H); $^{13}$C NMR (150 MHz, DMSO-d$_6$) δ 170.9, 160.6, 151.3, 148.6, 148.4, 145.5, 138.3, 128.6 (2C), 127.0 (2C), 123.3, 122.5, 113.1, 37.6, 36.0, 32.4 (2C), 25.0 (2C). The latter was obtained as a pale brown solid. HRMS m/z (ESI) calcd for $C_{20}H_{19}N_6O_4$ (M+H)$^+$ 407.1468, found 407.1465, in agreement with the calculated value from ChemDraw: MW=406.4020, Exact mass=406.1390; $^1$H NMR (600 MHz, DMSO-d$_6$) δ 12.27 (s, 1H), 7.51 (d, J=8.8 Hz, 2H), 7.33-7.27 (m, 3H), 2.48 (d, J=7.4 Hz, 2H), 2.24-2.17 (m, 1H), 1.72-1.67 (m, 2H), 1.64-1.58 (m, 2H), 1.53-1.47 (m, 2H), 1.20-1.14 (m, 2H); $^{13}$C NMR (150 MHz, DMSO-d$_6$) δ160.9, 156.4, 152.8, 148.5, 147.4, 136.6, 129.1, 127.8 (2C), 124.1, 122.6, 121.2 (2C), 113.3, 37.7, 35.6, 32.4 (2C), 25.0 (2C).

Compound 7 was prepared from 2-cyclopentylacetic acid, 3,6-dichloropyridazine, and 2-fluoro-4-aminophenol in a similar manner to that of Example 2. It was obtained as a pale yellow solid. HRMS m/z (ESI) calcd for $C_{20}H_{18}FN_6O_4$ (M+H)$^+$ 425.1374, found 425.01370, in agreement with the calculated value from ChemDraw: MW=424.3924, Exact mass=424.1295; $^1$H NMR (600 MHz, DMSO-d$_6$) δ 13.14 (s, 1H), 12.22 (s, 1H), 7.61-7.51 (m, 2H), 7.44-7.37 (m, 2H), 2.49 (s, 2H), 2.22 (hept, J=7.2 Hz, 1H), 1.73-1.68 (m, 2H), 1.65-1.59 (m, 2H), 1.55-1.46 (m, 2H), 1.21-1.15 (m, 2H); $^{13}$C NMR (150 MHz, DMSO-d$_6$) δ 160.7, 155.9, 153.3 (J=246 Hz), 152.4, 148.1, 147.8, 140.5 (J=12 Hz), 137.5 (J=9 Hz), 124.3, 123.2 (J=3 Hz), 123.0 (J=7.5 Hz), 115.4, 115.2, 113.0, 37.7, 35.9, 32.4 (2C), 25.0 (2C).

Compound 8 was prepared from 2-cyclopentylacetic acid, 3,6-dichloropyridazine, and 2-chloro-4-aminophenol in a similar manner to that of Example 1. It was obtained as a gray solid. HRMS m/z (ESI) calcd for $C_{20}H_{18}ClN_6O_4$ (M+H)$^+$ 441.1078, found 441.1068, in agreement with the calculated value from ChemDraw: MW=440.8440, Exact mass=440.1000; $^1$H NMR (400 MHz, DMSO-d$_6$) δ 12.23 (s, 1H), 7.76-7.73 (m, 1H), 7.54 (s, 2H), 7.41 (s, 1H), 2.50 (d, J=7.2 Hz, 2H), 2.27-2.18 (m, 1H), 1.74-1.66 (m, 2H), 1.65-1.58 (m, 2H), 1.56-1.45 (m, 2H), 1.21-1.14 (m, 2H); $^{13}$C NMR (150 MHz, DMSO-d$_6$) δ 160.7, 156.1, 152.5, 149.4, 148.4, 147.9, 137.7, 128.1, 126.7, 126.0, 124.3, 123.3, 123.0, 113.1, 37.7, 35.9, 32.4 (2C), 25.0 (2C).

Compound 9 was prepared from 2-cyclopentylacetic acid, 3,6-dichloropyridazine, and 2-bromo-4-aminophenol in a similar manner to that of Example 1. It was obtained as a pale yellow solid. HRMS m/z (ESI) calcd for $C_{20}H_{18}BrN_6O_4$ (M+H)$^+$ 485.0573, found 485.0580, in agreement with the calculated value from ChemDraw: MW=485.2980, Exact mass=484.0495; $^1$H NMR (600 MHz, DMSO-d$_6$) δ 12.20 (s, 1H), 7.85 (d, J=2.4 Hz, 1H), 7.56 (dd, J=9.0, 2.4 Hz, 1H), 7.49 (d, J=9.0 Hz, 1H), 7.40 (s, 1H), 2.49 (d, J=7.2 Hz, 2H), 2.25-2.19 (m, 1H), 1.72-1.68 (m, 2H), 1.65-1.60 (m, 2H), 1.53-1.50 (m, 2H), 1.21-1.16 (m, 2H); $^{13}$C NMR (150 MHz, DMSO-d$_6$) δ 160.6, 157.8, 152.5, 150.3, 149.5, 147.8, 138.4, 130.9, 127.1, 124.1, 123.4, 122.8, 115.3, 113.7, 37.7, 35.9, 32.4 (2C), 25.0 (2C).

Compound 10 was prepared from 2-cyclopentylacetic acid, 3,6-dichloropyridazine, and 3-chloro-4-aminophenol in a similar manner to that of Example 1. It was obtained as a pale yellow solid. HRMS m/z (ESI) calcd for $C_{20}H_{18}BrN_6O_4$ (M+H)$^+$ 441.1078, found 441.1070, in agreement with the calculated value from ChemDraw: MW=440.8440, Exact mass=440.1000; $^1$H NMR (600 MHz, DMSO-d$_6$) δ 13.33 (s, 1H), 12.32 (s, 1H), 7.69-7.59 (m, 2H), 7.36 (dd, J=8.4, 2.4 Hz, 1H), 7.33 (s, 1H), 2.49 (d, J=7.2 Hz, 2H), 2.21 (hept, J=7.2 Hz, 1H), 1.72-1.68 (m, 2H), 1.65-1.58 (m, 2H), 1.55-1.45 (m, 2H), 1.20-1.15 (m, 2H); $^{13}$C NMR (150 MHz, DMSO-d$_6$) δ 160.8, 156.0, 155.3, 152.5, 148.0, 147.6, 133.7, 132.3, 131.3, 124.1, 123.8, 122.5, 120.8, 113.0, 37.7, 35.9, 32.4, 25.0.

Compound 11 was prepared from 2-cyclopentylacetic acid, 3,6-dichloropyridazine, and 2,5-dichloro-4-aminophenol in a similar manner to that of Example 1. It was obtained as a pale brown solid. HRMS m/z (ESI) calcd for $C_{20}H_{17}Cl_2N_6O_4$ (M+H)$^+$ 475.0688, found 475.0691, in agreement with the calculated value from ChemDraw: MW=475.2860, Exact mass=474.0610; $^1$H NMR (600 MHz, DMSO-d$_6$) δ 12.25 (s, 1H), 7.92 (s, 1H), 7.88 (s, 1H), 7.43 (s, 1H), 2.50 (d, J=7.2 Hz, 2H), 2.26-2.18 (m, 1H), 1.72-1.68 (m, 2H), 1.65-1.60 (m, 2H), 1.54-1.48 (m, 2H), 1.21-1.16 (m, 2H); $^{13}$C NMR (150 MHz, DMSO-d$_6$) δ 160.7, 160.0, 152.3, 151.1, 150.1, 148.0, 136.6, 131.5, 131.3, 125.3, 125.2, 123.2, 123.2, 114.2, 37.7, 35.9, 32.4 (2C), 25.0 (2C).

Compound 12 was prepared from 2-cyclopentylacetic acid, 3,6-dichloropyridazine, and 2-methoxy-4-aminophenol in a similar manner to that of Example 1. It was obtained as a white solid. HRMS m/z (ESI) calcd for $C_{21}H_{21}N_6O_5$ (M+H)$^+$ 437.1573, found 437.1570, in agreement with the calculated value from ChemDraw: MW=436.4280, Exact mass=436.1495; $^1$H NMR (400 MHz, DMSO-d$_6$) δ 13.07 (s, 1H), 12.07 (s, 1H), 7.34-7.30 (m, 2H), 7.26 (d, J=2.4 Hz, 1H), 7.09 (dd, J=8.4, 2.4 Hz, 1H), 3.75 (s, 3H), 2.48 (d, J=15.0 Hz, 2H), 2.25-2.17 (m, 1H), 1.71-1.67 (m, 2H), 1.65-1.59 (m, 2H), 1.54-1.47 (m, 2H), 1.21-1.15 (m, 2H); $^{13}$C NMR (150 MHz, DMSO-d$_6$) δ 160.7, 156.2, 152.9, 151.4, 148.3, 147.2, 142.1, 137.8, 123.3, 123.2, 122.5, 119.1, 113.2, 111.7, 56.5, 37.7, 35.7, 32.4 (2C), 25.0 (2C).

Compound 14 was prepared from 4-methylvaleric acid, 3,6-dichloropyridazine, and 2,6-dichloro-4-aminophenol in a similar manner to that of Example 1. It was obtained as a pale yellow solid. HRMS m/z (ESI) calcd for $C_{18}H_{15}Cl_2N_6O_4$ (M+H)$^+$ 449.0532, found 449.0528, in agreement with the calculated value from ChemDraw: MW=449.2480, Exact mass=448.0454; $^1$H NMR (600 MHz, DMSO-d$_6$) δ 13.22 (s, 1H), 12.17 (s, 1H), 7.72 (s, 2H), 7.43 (s, 1H), 2.34 (d, J=7.2 Hz, 2H), 1.99-1.92 (m, 1H), 0.84 (d, J=6.6 Hz, 6H); $^{13}$C NMR (150 MHz, DMSO-d$_6$) δ 160.6, 155.0, 151.2, 147.8, 147.4, 145.8, 137.7, 128.8 (2C), 127.1 (2C), 123.3, 123.1, 112.6, 38.9, 26.6, 22.7 (2C).

Compound 15 was prepared from 4-methylvaleric acid, 3,6-dichloropyridazine, and 2-bromo-4-aminophenol in a similar manner to that of Example 1. It was obtained as a pale brown solid. HRMS m/z (ESI) calcd for $C_{181}H_{16}BrN_6O_4$ (M+H)$^+$ 459.0416, found 459.0416, in agreement with the calculated value from ChemDraw: MW=459.2600, Exact mass=458.0338; $^1$H NMR (600 MHz, DMSO-d$_6$) δ 13.21 (s, 1H), 12.21 (s, 1H), 7.85 (d, J=2.4 Hz, 1H), 7.56 (dd, J=8.4, 2.4 Hz, 1H), 7.51 (d, J=8.4 Hz, 1H), 7.38 (s, 1H), 2.39 (d, J=7.2 Hz, 2H), 2.05-1.96 (m, 1H), 0.91 (d, J=7.2 Hz, 6H); $^{13}$C NMR (150 MHz, DMSO-d$_6$) δ 160.7, 156.6, 152.5, 150.6, 148.7, 147.2, 138.0, 131.0, 127.2, 124.2, 124.0, 122.9, 115.3, 113.3, 38.9, 26.6, 22.7 (2C).

Compound 16 was prepared from 4-methylvaleric acid, 3,6-dichloropyridazine, and 2,5-dichloro-4-aminophenol in a similar manner to that of Example 1. It was obtained as a pale brown solid. HRMS m/z (ESI) calcd for $C_{18}H_{15}Cl_2N_6O_4$ (M+H)+ 449.0532, found 449.0525, in agreement with the calculated value from ChemDraw: MW=449.2480, Exact mass=448.0454; $^1$H NMR (600 MHz, DMSO-$d_6$) δ 12.25 (s, 1H), 7.91 (s, 1H), 7.90 (s, 1H), 7.41 (s, 1H), 2.39 (d, J=7.2 Hz, 2H), 2.05-2.00 (m, 1H), 0.91 (d, J=7.2 Hz, 6H); $^{13}$C NMR (150 MHz, DMSO-$d_6$) δ 160.7, 156.5, 152.4, 150.3, 148.6, 147.4, 138.1, 131.5, 131.3, 130.1, 125.3, 125.2, 123.8, 122.1, 38.9, 26.7, 22.7 (2C).

Compound 17 was prepared from 4-methylvaleric acid, 3,6-dichloropyridazine, and 2-methoxy-4-aminophenol in a similar manner to that of Example 1. It was obtained as a pale yellow solid. HRMS m/z (ESI) calcd for $C_{19}H_{19}N_6O_5$ (M+H)+ 411.1417, found 471.1401, in agreement with the calculated value from ChemDraw: MW=410.3900, Exact mass=410.1339; $^1$H NMR (400 MHz, DMSO-$d_6$) δ 13.08 (s, 1H), 12.07 (s, 1H), 7.34 (d, J=8.4 Hz, 1H), 7.30 (s, 1H), 7.26 (d, J=2.4 Hz, 1H), 7.10 (dd, J=8.4, 2.4 Hz, 1H), 3.75 (s, 3H), 2.37 (d, J=7.2 Hz, 2H), 2.06-1.97 (m, 1H), 0.90 (d, J=7.2 Hz, 6H); $^{13}$C NMR (150 MHz, DMSO-$d_6$) δ 160.7, 155.3, 152.9, 151.4, 147.7, 146.6, 142.2, 137.6, 123.9, 123.2, 122.5, 119.1, 112.9, 111.7, 56.6, 26.7, 22.7 (2C).

Compound 18 was prepared from 4,4-dimethylvaleric acid, 3,6-dichloropyridazine, and 2,6-dichloro-4-aminophenol in a similar manner to that of Example 1. It was obtained as a pale yellow solid. HRMS m/z (ESI) calcd for $C_{19}H_{17}Cl_2N_6O_4$ (M+H)+ 463.0688, found 463.0684, in agreement with the calculated value from ChemDraw: MW=463.2750, Exact mass=462.0610; 1H NMR (600 MHz, Methanol-$d_4$) δ 7.66 (s, 2H), 7.27 (s, 1H), 2.52 (s, 2H), 0.92 (s, 9H); $^{13}$C NMR (150 MHz, Methanol-$d_4$) δ 162.0, 158.0, 151.8, 150.5, 145.9, 145.2, 138.6, 128.7 (2C), 125.7 (2C), 124.9, 123.4, 112.3, 41.4, 32.2, 28.4 (3C).

Compound 19 was prepared from 4,4-dimethylvaleric acid, 3,6-dichloropyridazine, and 2-chloro-4-aminophenol in a similar manner to that of Example 1. It was obtained as a white solid. HRMS m/z (ESI) calcd for $C_{19}H_{18}ClN_6O_4$ (M+H)+ 429.1078, found 429.1068, in agreement with the calculated value from ChemDraw: MW=428.8330, Exact mass=428.1000; $^1$H NMR (600 MHz, DMSO-$d_6$) δ 13.16 (s, 1H), 12.18 (s, 1H), 7.73 (s, 1H), 7.51 (s, 2H), 7.33 (s, 1H), 2.48 (s, 2H), 0.93 (s, 9H); $^{13}$C NMR (150 MHz, DMSO-$d_6$) δ 161.1, 159.2, 152.2, 150.7, 148.7, 145.7, 138.9, 127.9, 126.4, 125.7, 125.2, 124.0, 122.8, 114.3, 41.6, 32.8, 29.7 (3C).

Compound 20 was prepared from 4,4-dimethylvaleric acid, 3,6-dichloropyridazine, and 2,5-dichloro-4-aminophenol in a similar manner to that of Example 1. It was obtained as a pale yellow solid. HRMS m/z (ESI) calcd for $C_{19}H_{17}Cl_2N_6O_4$ (M+H)+ 463.0688, found 463.0677, in agreement with the calculated value from ChemDraw: MW=463.2750, Exact mass=462.0610; $^1$H NMR (600 MHz, DMSO-$d_6$) δ 12.24 (s, 1H), 7.94 (s, 1H), 7.92 (s, 1H), 7.36 (s, 1H), 2.49 (s, 2H), 0.94 (s, 9H); $^{13}$C NMR (150 MHz, DMSO-$d_6$) δ 161.2, 158.0, 152.0, 150.5, 149.5, 145.9, 135.7, 131.5, 131.3, 125.4, 125.3, 125.2, 123.7, 113.7, 41.7, 32.9, 29.7 (3C).

Compound 21 was prepared from 4,4-dimethylvaleric acid, 3,6-dichloropyridazine, and 2-methoxy-4-aminophenol in a similar manner to that of Example 1. It was obtained as a pale brown solid. HRMS m/z (ESI) calcd for $C_{20}H_{21}N_6O_5$ (M+H)+ 425.1573, found 425.1577, in agreement with the calculated value from ChemDraw: MW=424.4170, Exact mass=424.1495; $^1$H NMR (600 MHz, DMSO-$d_6$) δ 13.07 (s, 1H), 12.06 (s, 1H), 7.35 (d, J=8.4 Hz, 1H), 7.26 (d, J=2.4 Hz, 1H), 7.24 (s, 1H), 7.10 (dd, J=8.4, 2.4 Hz, 1H), 2.47 (s, 2H), 0.93 (s, 9H); $^{13}$C NMR (150 MHz, DMSO-$d_6$) δ 161.2, 155.5, 152.6, 151.4, 147.8, 145.1, 142.3, 137.6, 125.3, 123.2, 122.5, 119.1, 113.0, 111.8, 56.6, 41.6, 32.8, 29.7 (3C).

Compound 22 was prepared from 3,6-dichloro-4,5-dimethylpyridazine and 2,6-dichloro-4-aminophenol in a similar manner to that of Example 1. It was obtained as a pale yellow solid. HRMS m/z (ESI) calcd for $C_{16}H_{11}Cl_2N_6O_4$ (M+H)+ 421.0219, found 421.0215, in agreement with the calculated value from ChemDraw: MW=421.1940, Exact mass=420.0141; $^1$H NMR (600 MHz, DMSO-$d_6$) δ 13.28 (s, 1H), 12.14 (s, 1H), 7.78 (s, 2H), 2.30 (s, 3H), 2.11 (s, 3H); $^{13}$C NMR (150 MHz, DMSO-$d_6$) δ 160.6, 155.0, 150.7, 147.4, 146.2, 140.6, 137.6, 131.9, 128.8 (2C), 127.1 (2C), 123.3, 112.6, 13.2, 12.9.

Compound 23 was prepared from 3,6-dichloro-4,5-dimethylpyridazine and 2-fluoro-4-aminophenol in a similar manner to that of Example 2. It was obtained as a pale yellow solid. HRMS m/z (ESI) calcd for $C_{16}H_{12}FN_6O_4$ (M+H)+ 371.0904, found 471.0410, in agreement with the calculated value from ChemDraw: MW=370.3004, Exact mass=370.0826; $^1$H NMR (600 MHz, DMSO-$d_6$) δ 12.10 (s, 1H), 7.56 (dd, J=11.4, 2.4 Hz, 1H), 7.49-7.45 (m, 1H), 7.40-7.35 (m, 1H), 2.24 (s, 3H), 2.09 (s, 3H); $^{13}$C NMR (150 MHz, DMSO-$d_6$) δ 160.6, 156.5, 153.3 (d, J=246 Hz), 152.0, 150.3, 148.5, 140.2, 139.9, 138.5, 132.4, 124.2, 122.9 (d, J=18 Hz), 115.1 (d, J=22.5 Hz), 114.1, 13.2, 12.8.

Compound 24 was prepared from 3,6-dichloro-4,5-dimethylpyridazine and 2-chloro-4-aminophenol in a similar manner to that of Example 1. It was obtained as a pale yellow solid. HRMS m/z (ESI) calcd for $C_{16}H_{12}ClN_6O_4$ (M+H)+ 387.0609, found 387.0605, in agreement with the calculated value from ChemDraw: MW=386.7520, Exact mass=386.0530; $^1$H NMR (600 MHz, DMSO-$d_6$) δ 13.16 (s, 1H), 12.12 (s, 1H), 7.74 (s, 1H), 7.54 (s, 2H), 2.25 (s, 3H), 2.10 (s, 3H); $^{13}$C NMR (150 MHz, DMSO-$d_6$) δ 160.6, 155.2, 152.0, 149.8, 147.6, 140.0, 137.3, 132.6, 128.1, 126.7, 126.0, 124.5, 123.0, 112.8, 13.2, 12.9.

Compound 25 was prepared from isobutyric acid, 3,6-dichloropyridazine, and 2-fluoro-4-aminophenol in a similar manner to that of Example 2. It was obtained as a white solid. HRMS m/z (ESI) calcd for $C_{17}H_{14}FN_6O_4$ (M+H)+ 385.1061, found 385.1057, in agreement with the calculated value from ChemDraw: MW=384.3274, Exact mass=384.0982; $^1$H NMR (600 MHz, DMSO-$d_6$) δ 13.15 (s, 1H), 12.23 (s, 1H), 7.58 (dd, J=11.4, 2.4 Hz, 1H), 7.54 (t, J=8.4 Hz, 1H), 7.42-7.38 (m, 1H), 7.34 (s, 1H), 3.04 (hept, J=7.2 Hz, 1H), 1.19 (d, J=7.2 Hz, 6H); $^{13}$C NMR (150 MHz, DMSO-$d_6$) δ 160.1, 156.5, 153.7, 153.4 (d, J=246.0 Hz), 152.7, 148.5, 140.3 (d, J=12.0 Hz), 137.8 (d, J=9.0 Hz), 124.4, 123.2, 123.0, 120.4, 115.3 (d, J=22.5 Hz), 113.3, 28.1, 20.9 (2C).

Compound 26 was prepared from isobutyric acid, 3,6-dichloropyridazine, and 2-chloro-4-aminophenol in a similar manner to that of Example 1. It was obtained as a pale yellow solid. HRMS m/z (ESI) calcd for $C_{17}H_{14}ClN_6O_4$ (M+H)+ 401.0765, found 401.0762, in agreement with the calculated value from ChemDraw: MW=400.7790, Exact mass=400.0687; $^1$H NMR (600 MHz, DMSO-$d_6$) δ 12.21 (s, 1H), 7.74 (d, J=1.8 Hz, 1H), 7.54-7.49 (m, 2H), 7.34 (s, 1H), 3.05 (hept, J=7.2 Hz, 1H), 1.19 (d, J=7.2 Hz, 6H); $^{13}$C NMR (150 MHz, DMSO-$d_6$) δ 160.0, 158.3, 153.7, 152.9, 150.0, 148.8, 138.5, 128.0, 126.5, 125.9, 124.2, 122.9, 120.5, 113.9, 28.1, 21.0 (2C).

Compound 27 was prepared from isobutyric acid, 3,6-dichloropyridazine, and 2-bromo-4-aminophenol in a similar manner to that of Example 1. It was obtained as a pale brown solid. HRMS m/z (ESI) calcd for $C_{17}H_{14}BrN_6O_4$ (M+H)⁺ 445.0260, found 445.0264, in agreement with the calculated value from ChemDraw: MW=445.2330, Exact mass=444.0182; ¹H NMR (600 MHz, DMSO-d₆) δ 12.21 (s, 1H), 7.86 (d, J=2.4 Hz, 1H), 7.56 (dd, J=8.4, 2.4 Hz, 1H), 7.49 (d, J=8.4 Hz, 1H), 7.34 (s, 1H), 3.05 (hept, J=7.2 Hz, 2H), 1.19 (d, J=7.2 Hz, 6H); ¹³C NMR (150 MHz, DMSO-d₆) δ 160.0, 157.8, 153.7, 152.9, 150.3, 149.5, 138.5, 136.7, 127.1, 124.1, 122.9, 120.7, 115.5, 113.7, 28.1, 21.0 (2C).

Compound 28 was prepared from isobutyric acid, 3,6-dichloropyridazine, and 2,6-dibromo-4-aminophenol in a similar manner to that of Example 1. It was obtained as a pale yellow solid. HRMS m/z (ESI) calcd for C₁₇H₁₃Br₂N₆O₄ (M+H)⁺ 522.9365, found 522.9364, in agreement with the calculated value from ChemDraw: MW=524.1290, Exact mass=521.9287; ¹H NMR (600 MHz, DMSO-d₆) δ 13.22 (s, 1H), 12.22 (s, 1H), 7.92 (s, 2H), 7.44 (s, 1H), 3.05 (hept, J=7.2 Hz, 1H), 1.20 (d, J=7.2 Hz, 6H); ¹³C NMR (150 MHz, DMSO-d₆) δ 160.0, 157.2, 154.3, 151.6, 149.1 147.6, 139.1, 130.4, 123.2 (2C), 120.1 (2C), 117.6, 113.4, 28.2, 21.0 (2C).

Compounds 29 and 35 were prepared from isobutyric acid, 3,6-dichloropyridazine, and 2,5-dichloro-4-aminophenol in a similar manner to that of Example 1. The former was obtained as a white solid. HRMS m/z (ESI) calcd for C₁₇H₁₃Cl₂N₆O₄ (M+H)⁺ 435.0375, found 435.0380, in agreement with the calculated value from ChemDraw: MW=435.2210, Exact mass=434.0297; ¹H NMR (600 MHz, DMSO-d₆) δ 13.31 (s, 1H), 12.28 (s, 1H), 7.97 (s, 1H), 7.93 (s, 1H), 7.37 (s, 1H), 3.05 (hept, J=7.2 Hz, 1H), 1.19 (d, J=7.2 Hz, 6H); ¹³C NMR (150 MHz, DMSO-d₆) δ 160.1, 155.3, 153.9, 152.6, 150.8, 147.4, 134.7, 131.5, 131.3, 125.6, 125.5, 124.3, 120.5, 112.6, 28.1, 20.9 (2C). The latter was obtained as a pale yellow solid. HRMS m/z (ESI) calcd for C₁₇H₁₃Cl₂N₆O₄ (M+H)⁺ 435.0375, found 435.0377, in agreement with the calculated value from ChemDraw: MW=435.2210, Exact mass=434.0297; ¹H NMR (600 MHz, DMSO-d₆) δ 13.33 (s, 1H), 12.22 (s, 1H), 8.02 (s, 1H), 7.94 (s, 1H), 6.86 (s, 1H), 3.06 (hept, J=7.2 Hz, 1H), 1.29 (d, J=7.2 Hz, 6H); ¹³C NMR (150 MHz, DMSO-d₆) δ 160.8, 155.0, 151.3, 150.9, 147.2, 147.1, 134.6, 131.4, 131.3, 128.4, 125.8, 125.7, 124.3, 112.5, 28.2, 21.2 (2C).

Compounds 30 and 36 were prepared from isobutyric acid, 3,6-dichloropyridazine, and 3-chloro-4-aminophenol in a similar manner to that of Example 1. The former was obtained as a pale yellow solid. HRMS m/z (ESI) calcd for C₁₇H₁₄ClN₆O₄ (M+H)⁺ 401.0765, found 401.0767, in agreement with the calculated value from ChemDraw: MW=400.7790, Exact mass=400.0687; ¹H NMR (400 MHz, DMSO-d₆) δ 13.22 (s, 1H), 12.32 (s, 1H), 7.70-7.62 (m, 2H), 7.38 (dd, J=8.4, 2.4 Hz, 1H), 7.27 (s, 1H), 3.04 (hept, J=7.2 Hz, 1H), 1.18 (d, J=7.2 Hz, 6H); 13C NMR (100 MHz, DMSO-d₆) δ 160.2, 155.4, 155.2, 153.5, 152.9, 147.3, 133.4, 132.3, 131.3, 124.0, 122.7, 121.3, 121.0, 112.7, 28.0, 20.9 (2C). The latter was obtained as a white solid. HRMS m/z (ESI) calcd for C₁₇H₁₄ClN₆O₄ (M+H)⁺ 401.0765, found 401.0767, in agreement with the calculated value from ChemDraw: MW=400.7790, Exact mass=400.0687; ¹H NMR (400 MHz, DMSO-d₆) δ 12.24 (s, 1H), 7.66 (d, J=2.4 Hz, 1H), 7.62 (d, J=8.4 Hz, 1H), 7.37 (dd, J=8.4, 2.4 Hz, 1H), 6.82 (s, 1H), 3.00 (hept, J=7.2 Hz, 2H), 1.24 (d, J=7.2 Hz, 6H); ¹³C NMR (100 MHz, DMSO-d₆) δ 160.9, 158.2, 155.0, 151.9, 149.8, 147.8, 134.7, 132.3, 131.3, 128.1, 123.3, 122.9, 121.2, 113.7, 28.0, 21.3 (2C).

Compound 31 was prepared from isobutyric acid, 3,6-dichloropyridazine, and 2-methoxy-4-aminophenol in a similar manner to that of Example 1. It was obtained as a pale brown solid. HRMS m/z (ESI) calcd for C₁₈H₁₇N₆O₅ (M+H)⁺ 397.1260, found 397.1251, in agreement with the calculated value from ChemDraw: MW=396.3630, Exact mass=396.1182; ¹H NMR (600 MHz, DMSO-d₆) δ 13.07 (s, 1H), 12.09 (s, 1H), 7.34 (d, J=8.4 Hz, 1H), 7.30-7.26 (m, 2H), 7.10 (dd, J=8.4, 2.4 Hz, 1H), 3.76 (s, 3H), 3.02 (hept, J=7.2 Hz, 1H), 1.18 (d, J=7.2 Hz, 6H); ¹³C NMR (150 MHz, DMSO-d₆) δ 160.1, 155.3, 153.2, 153.1, 151.6, 147.7, 142.0, 137.6, 123.4, 122.6, 120.6, 119.2, 112.9, 111.7, 56.6, 28.0, 21.0 (2C).

Compound 32 was prepared from cyclopentanecarboxylic acid, 3,6-dichloropyridazine, and 2-fluoro-4-aminophenol in a similar manner to that of Example 2. It was obtained as a pale yellow solid. HRMS m/z (ESI) calcd for C₁₉H₁₆FN₆O₄ (M+H)⁺ 411.1217, found 411.1213, in agreement with the calculated value from ChemDraw: MW=410.3654, Exact mass=410.1139; ¹H NMR (600 MHz, DMSO-d₆) δ 13.05 (s, 1H), 12.20 (s, 1H), 7.59-7.52 (m, 2H), 7.40 (d, J=8.4 Hz, 1H), 7.35 (s, 1H), 3.10 (p, J=8.4 Hz, 1H), 2.02-1.94 (m, 2H), 1.79-1.71 (m, 2H), 1.67-1.55 (m, 4H); ¹³C NMR (150 MHz, DMSO-d₆) δ 160.4, 155.5, 154.2, 153.4 (d, J=246.0 Hz), 151.7, 147.7, 140.6 (d, J=12.0 Hz), 137.4 (d, J=10.5 Hz), 124.5, 123.3, 123.0, 120.41, 115.3 (d, J=22.5 Hz), 112.9, 56.5, 31.3 (2C), 25.3 (2C).

Compound 33 was prepared from cyclopentanecarboxylic acid, 3,6-dichloropyridazine, and 3-chloro-4-aminophenol in a similar manner to that of Example 1. It was obtained as a pale yellow solid. HRMS m/z (ESI) calcd for C₁₉H₁₆ClN₆O₄ (M+H)⁺ 427.0922, found 427.0914, in agreement with the calculated value from ChemDraw: MW=426.8170, Exact mass=426.0843; ¹H NMR (400 MHz, DMSO-d₆) δ 12.28 (s, 1H), 7.61 (d, J=8.4 Hz, 2H), 7.34 (dd, J=8.4, 2.4 Hz, 1H), 7.28 (s, 1H), 3.10 (p, J=8.4 Hz, 1H), 2.01-1.90 (m, 2H), 1.79-1.70 (m, 2H), 1.70-1.50 (m, 4H); ¹³C NMR (150 MHz, DMSO-d₆) δ 160.5, 155.5, 155.0, 152.7, 151.5, 147.8, 133.5, 132.3, 131.3, 123.7, 122.6, 121.4, 120.9, 112.8, 56.5, 31.3 (2C), 25.3 (2C).

Compound 34 was prepared from cyclopentanecarboxylic acid, 3,6-dichloropyridazine, and 2,5-dichloro-4-aminophenol in a similar manner to that of Example 1. It was obtained as a pale brown solid. HRMS m/z (ESI) calcd for C₁₉H₁₅Cl₂N₆O₄ (M+H)⁺ 461.0532, found 461.0528, in agreement with the calculated value from ChemDraw: MW=461.2590, Exact mass=460.0454; ¹H NMR (600 MHz, DMSO-d₆) δ 12.23 (s, 1H), 7.91 (s, 1H), 7.89 (s, 1H), 7.38 (s, 1H), 3.14-3.08 (m, 1H), 2.00-1.92 (m, 2H), 1.79-1.71 (m, 2H), 1.67-1.55 (m, 4H); ¹³C NMR (150 MHz, DMSO-d₆) δ 160.1, 155.3, 153.9, 152.6, 150.8, 147.4, 134.7, 131.5, 131.3, 125.6, 125.5, 124.3, 120.5, 112.6, 56.5, 31.3 (2C), 25.3 (2C).

Compound 37 was prepared from cyclopropanecarboxylic acid, 3,6-dichloropyridazine, and 2-chloro-4-aminophenol in a similar manner to that of Example 1. It was obtained as a white solid. HRMS m/z (ESI) calcd for C₁₇H₁₂ClN₆O₄ (M+H)⁺ 399.0609, found 399.0597, in agreement with the calculated value from ChemDraw: MW=398.7630, Exact mass=398.0530; ¹H NMR (400 MHz, DMSO-d₆) δ 13.20 (s, 1H), 12.10 (s, 1H), 7.76 (d, J=2.4 Hz, 1H), 7.61 (d, J=8.4 Hz, 1H), 7.55 (dd, J=8.4, 2.4 Hz, 1H), 6.59 (s, 1H), 2.07-1.99 (m, 1H), 1.15-1.06 (m, 2H), 1.01-0.93 (m, 2H); ¹³C NMR (100 MHz, DMSO-d₆) δ 160.7, 155.2, 151.9, 149.8, 147.6, 144.3, 137.4, 128.2, 126.7, 126.0, 125.6, 124.6, 123.0, 112.8, 13.5, 10.0 (2C).

Compound 38 was prepared from cyclopentanecarboxylic acid, 3,6-dichloropyridazine, and 2,6-dichloro-4-aminophenol in a similar manner to that of Example 1. It was obtained as a pale brown solid. HRMS m/z (ESI) calcd for C₁₉H₁₅Cl₂N₆O₄ (M+H)⁺ 461.0532, found 461.0530, in agreement with the calculated value from ChemDraw: MW=461.2590, Exact mass=460.0454; $^1$H NMR (600 MHz, DMSO-d$_6$) δ 12.14 (s, 1H), 7.78 (s, 2H), 6.86 (s, 1H), 3.17 (p, J=7.2 Hz, 1H), 2.14-2.04 (m, 2H), 1.81-1.63 (m, 6H); $^{13}$C NMR (150 MHz, DMSO-d$_6$) δ 162.6, 160.6, 153.2, 150.5, 144.3, 144.1, 140.6, 128.7, 127.9 (2C), 126.5 (2C), 123.1, 115.4, 56.5, 31.4 (2C), 25.3 (2C).

Compound 39 was prepared from cyclopentanecarboxylic acid, 3,6-dichloropyridazine, and 2-chloro-4-aminophenol in a similar manner to that of Example 1. It was obtained as a pale yellow solid. HRMS m/z (ESI) calcd for $C_{19}H_{16}ClN_6O_4$ (M+H)$^+$ 427.0922, found 427.0917, in agreement with the calculated value from ChemDraw: MW=426.8170, Exact mass=426.0843; $^1$H NMR (600 MHz, DMSO-d$_6$) δ 12.19 (s, 1H), 7.58 (d, J=2.4 Hz, 1H), 7.55 (d, J=8.4 Hz, 1H), 7.30 (dd, J=8.4, 2.4 Hz, 1H), 6.80 (s, 1H), 3.12-3.05 (m, 1H), 2.04-2.00 (m, 2H), 1.76-1.71 (m, 2H), 1.68-1.59 (m, 4H); $^{13}$C NMR (150 MHz, DMSO-d$_6$) δ 160.7, 154.4, 154.0, 152.4, 145.8, 133.5, 132.4, 131.2, 128.0, 123.8, 122.7, 121.4, 120.9, 112.8, 56.5, 31.5 (2C), 25.3 (2C).

Compound 40 was prepared from isobutyric acid, 3,6-dichloropyridazine, and 2,5-dichloro-4-aminophenol in a similar manner to that of Example 3. It was obtained as a white solid. HRMS m/z (ESI) calcd for $C_{18}H_{14}Cl_2N_5O_4$ (M+H)$^+$ 434.0423, found 434.0425, in agreement with the calculated value from ChemDraw: MW=434.2330, Exact mass=433.0345; $^1$H NMR (600 MHz, DMSO-d$_6$) δ 12.44 (s, 1H), 12.30 (s, 1H), 8.91 (s, 1H), 8.07 (s, 1H), 7.98 (s, 1H), 7.37 (s, 1H), 3.05 (hept, J=7.2 Hz, 1H), 1.19 (d, J=7.2 Hz, 6H); $^{13}$C NMR (150 MHz, DMSO-d$_6$) δ 160.7, 160.1, 154.8, 153.9, 152.6, 150.6, 149.0, 133.1, 132.1, 131.6, 125.5, 125.3, 120.5, 114.1, 89.6, 28.1, 20.9 (2C).

Compound 41 was prepared from isobutyric acid, 3,6-dichloropyridazine, and 2-chloro-4-aminophenol in a similar manner to that of Example 3. It was obtained as a pale yellow solid. HRMS m/z (ESI) calcd for $C_{18}H_{15}ClN_5O_4$ (M+H)$^+$ 400.0813, found 400.0811, in agreement with the calculated value from ChemDraw: MW=399.7910, Exact mass=399.0734; $^1$H NMR (400 MHz, DMSO-d$_6$) δ 13.22 (s, 1H), 12.32 (s, 1H), 8.90 (s, 1H), 7.70-7.62 (m, 2H), 7.38 (dd, J=8.4, 2.4 Hz, 1H), 7.27 (s, 1H), 3.04 (hept, J=7.2 Hz, 1H), 1.18 (d, J=7.2 Hz, 6H); 13C NMR (100 MHz, DMSO-d$_6$) δ 160.2, 155.4, 155.2, 153.5, 152.9, 150.6, 147.3, 133.4, 132.3, 131.3, 124.0, 122.7, 121.3, 121.0, 112.7, 28.0, 20.9 (2C).

Compound 43 was prepared from 4,4-dimethylvaleric acid, 3,6-dichloropyridazine, and 2,6-dichloro-4-aminophenol in a similar manner to that of Example 3. It was obtained as a pale yellow solid. HRMS m/z (ESI) calcd for $C_{20}H_{18}Cl_2N_5O_4$ (M+H)$^+$ 462.0736, found 471.0410, in agreement with the calculated value from ChemDraw: MW=462.2870, Exact mass=461.0658; $^1$H NMR (600 MHz, DMSO-d$_6$) δ 12.30 (s, 1H), 12.24 (s, 1H), 8.89 (s, 1H), 7.88 (s, 2H), 7.45 (s, 1H), 2.51 (s, 2H), 0.94 (s, 9H); $^{13}$C NMR (150 MHz, DMSO-d$_6$) δ 161.2, 160.9, 154.7, 151.0, 149.5, 146.3, 146.0, 136.4, 128.9 (2C), 128.6 (2C), 124.6, 114.4, 89.2, 41.7, 32.8, 29.7 (3C).

Compound 44 was prepared from 4,4-dimethylvaleric acid, 3,6-dichloropyridazine, and 2,5-dichloro-4-aminophenol in a similar manner to that of Example 3. It was obtained as a pale yellow solid. HRMS m/z (ESI) calcd for $C_{20}H_{18}Cl_2N_5O_4$ (M+H)$^+$ 462.0736, found 471.0410, in agreement with the calculated value from ChemDraw: MW=462.2870, Exact mass=461.0658; $^1$H NMR (600 MHz, DMSO-d$_6$) δ 11.76 (s, 1H), 11.55 (s, 1H), 8.79 (s, 1H), 8.49 (s, 1H), 7.74 (s, 1H), 7.28 (s, 1H), 2.47 (s, 2H), 0.92 (s, 9H); $^{13}$C NMR (150 MHz, DMSO-d$_6$) δ 182.0, 176.8, 167.8, 161.2, 152.3, 151.9, 145.6, 144.0, 134.4, 125.1, 124.9, 122.6, 121.4, 121.2, 78.9, 41.6, 32.8, 29.7 (3C).

Compound 45 was prepared from 4,4-dimethylvaleric acid, 3,6-dichloropyridazine, and 3-chloro-4-aminophenol in a similar manner to that of Example 3. It was obtained as a white solid. HRMS m/z (ESI) calcd for $C_{20}H_{19}ClN_5O_4$ (M+H)$^+$ 428.1126, found 428.1130, in agreement with the calculated value from ChemDraw: MW=427.8450, Exact mass=427.1047; $^1$H NMR (400 MHz, DMSO-d$_6$) δ 12.21 (s, 2H), 8.86 (s, 1H), 7.82 (d, J=2.4 Hz, 1H), 7.60-7.52 (m, 2H), 7.34 (s, 1H), 2.49 (s, 2H), 0.94 (s, 9H); $^{13}$C NMR (150 MHz, DMSO-d$_6$) δ 161.2, 161.0, 154.9, 152.1, 149.8, 149.7, 145.9, 136.0, 129.8, 128.2, 126.1, 125.3, 124.4, 114.5, 89.0, 41.6, 32.9, 29.7 (3C).

Compound 46 was prepared from 3,6-dichloro-4,5-dimethylpyridazine and 2-methoxy-4-aminophenol in a similar manner to that of Example 1. It was obtained as a pale yellow solid. HRMS m/z (ESI) calcd for $C_{17}H_{15}N_6O_5$ (M+H)$^+$ 383.1104, found 383.1106, in agreement with the calculated value from ChemDraw: MW=382.3360, Exact mass=382.1026; $^1$H NMR (600 MHz, DMSO-d$_6$) δ 13.07 (s, 1H), 11.96 (s, 1H), 7.31 (d, J=8.4 Hz, 1H), 7.25 (d, J=2.4 Hz, 1H), 7.10 (dd, J=8.4, 2.4 Hz, 1H), 2.50 (s, 3H), 2.22 (s, 3H), 2.08 (s, 3H); $^{13}$C NMR (150 MHz, DMSO-d$_6$) δ 160.6, 155.3, 152.4, 151.4, 147.6, 142.6, 139.4, 137.5, 132.7, 123.3, 122.5, 119.1, 112.9, 111.7, 56.6, 13.3, 12.8.

Compound 48 was prepared from pivalic acid, 3,6-dichloropyridazine, and 2,6-dichloro-4-aminophenol in a similar manner to that of Example 4. HRMS m/z (ESI) calcd for $C_{19}H_{18}Cl_2N_3O_4$ (M+H)$^+$ 422.0674, found 422.0678, in agreement with the calculated value from ChemDraw: MW=422.2620, Exact mass=421.0596; $^1$H NMR (600 MHz, DMSO-d$_6$) δ 13.18 (s, 1H), 11.10 (s, 1H), 10.67 (s, 1H), 8.04 (s, 1H), 7.92 (s, 2H), 7.65 (s, 1H), 7.43 (s, 1H), 1.34 (s, 9H); $^{13}$C NMR (150 MHz, DMSO-d$_6$) δ 176.4, 163.1, 162.5, 151.3, 151.0, 150.3, 127.9, 125.9 (2C), 125.5 (2C), 123.6, 123.5, 122.7, 118.0, 35.8, 27.9 (3C).

Compound 50 was prepared from pivalic acid, 3,6-dichloropyridazine, and 2,6-dichloro-4-aminophenol in a similar manner to that of Example 5. HRMS m/z (ESI) calcd for $C_{18}H_{15}Cl_2N_6O_2$ (M+H)$^+$ 381.0634, found 381.0637, in agreement with the calculated value from ChemDraw: MW=381.2170, Exact mass=380.0555; $^1$H NMR (600 MHz, DMSO-d$_6$) δ 13.22 (s, 1H), 13.0 (s, 1H), 7.65 (s, 2H), 7.43 (s, 1H), 1.32 (s, 9H); $^{13}$C NMR (150 MHz, DMSO-d$_6$) 176.5, 163.0, 150.3, 127.9, 125.9 (2C), 125.5 (2C), 123.6, 123.5, 122.7, 35.7, 27.9 (3C).

Tests and Results

1) Tests on Pharmacological Characteristics of Compounds 1 to 50 and Results Thereof Activities of compounds of Formula (I) as THRα and THRβ agonists were determined by analogy to the procedures described in *J. Med. Chem.* 2014, 57, 3912. Test compound was dissolved and serially diluted in dimethyl sulfoxide (DMSO) with a final compound concentration of 60 mM. Buffer 1 (50 mM Hepes, pH 7.0, 1 mM DTT, 0.05% NP40, and 0.2 mg/mL BSA) was employed to prepare solutions of THRα (125 nM) and THRβ (50 nM). Buffer 1 was employed again to prepare EE-RxRα at the same concentrations as those of THRα and THRβ, respectively. Buffer 1+5% DMSO was employed to prepare biotin-GRIP (THRα: 250 mM, THRβ: 100 nM). Buffer 2 (50 mM Tris, pH 7.4, 100 mM NaCl, and 0.2 mg/mL BSA) was employed to prepare a mixed solution of 2×Eu-anti-GST and 2×streptavidin-d2. 5 µL of the THRα (THRβ) solution+5 µL of EE-RxRα+2.5 µL of the DMSO solution of test compound+2.5 µL of biotin-GRIP+5 µL of the mixed solution of 2×Eu-anti-GST and 2×streptavidin-d2 was employed as the reaction system, and incubated overnight at 4° C. Fluorescence was read at 665 nm and 615 nm using Synergy™ H1, and the fluorescence ratio of 665 nm/615 nm was calculated.

The results are shown in Table 1.

TABLE 1

Agonistic activities of test compounds toward THRa and THRβ receptors

| Code | $EC_{50}$ of THRα (µM) | $EC_{50}$ of THRβ (µM) |
|---|---|---|
| MGL-3196 | 0.1015 | 0.01046 |
| T3 | 0.006035 | 0.005431 |
| 1 | 0.126 | 0.101 |
| 2 | 5.378 | 0.021 |
| 3 | 1.396 | 0.810 |
| 4 | >60 | 1.574 |
| 5 | 0.883 | 4.900 |
| 6 | 2.755 | 0.09490 |
| 7 | 9.997 | 0.013 |
| 8 | 6.146 | 0.0326 |
| 9 | 4.758 | 0.642 |
| 10 | — | 1.523 |
| 11 | 2.143 | 0.372 |
| 12 | 8.675 | 0.723 |
| 13 | >60 | 1.902 |
| 14 | 3.3892 | 0.0254 |
| 15 | — | 1.515 |
| 16 | 0.003 | 17.56 |
| 17 | >60 | 0.0616 |
| 18 | 2.111 | 0.0311 |
| 19 | 11.83 | 0.0668 |
| 20 | — | 4.581 |
| 21 | 19.889 | 1.520 |
| 22 | 0.631 | 0.1841 |
| 23 | 4.587 | 0.776 |
| 24 | 3.287 | 0.0101 |
| 25 | 0.014 | 2.698 |
| 26 | 2.073 | 0.0550 |
| 27 | 2.550 | 0.0311 |
| 28 | 0.03810 | 0.1015 |
| 29 | — | 0.1166 |
| 30 | >60 | 17.31 |
| 31 | 5.109 | 0.0625 |
| 32 | 18.543 | 0.279 |
| 33 | — | 7.546 |
| 34 | 0.014 | 3.848 |
| 35 | >60 | >60 |
| 36 | 13.75 | 4.165 |
| 37 | 0.001 | 3.217 |
| 38 | 4.656 | 0.783 |
| 39 | 3.221 | 0.583 |
| 40 | 24.14 | >63 |
| 41 | 0.001 | >60 |
| 42 | 1.808 | 0.0257 |
| 43 | 6.623 | 0.0403 |
| 44 | 2.315 | 0.042 |
| 45 | — | >60 |
| 46 | 50.795 | 1.405 |
| 47 | 17.554 | 1.647 |
| 48 | 3.658 | 0.745 |
| 49 | 3.323 | 0.254 |
| 50 | 2.587 | 0.465 |

The results presented in Table 1 show that most of Compounds 1 to 50 were active as THRβ agonists, whereas the compounds exhibited weak activities toward THRα. Further, most of the compounds exhibited a higher selectivity to THRβ compared with MGL-3196 and prior art substituted pyridazinones. Due to these significant advantages, it is necessary to perform intensive studies on pharmacological characteristics of the compounds.

2) Assays with Normal Cell Lines (Mouse Fibroblast Cell Line L929) to Assess Cytotoxicity of the Compounds Concentration of L929 mouse fibroblasts was adjusted to $4 \times 10^5$ cells/mL. The cells were seeded in a 96 well plate with 10 µL per well. Wells not supplied with the cells (blank group) were provided. The cells were cultivated on the plate and were allowed to adhere overnight. Then, cell culture supernatants were collected, and 200 µL of test compound at various concentrations were added to the corresponding cell culture supernatants. Control and compound-treated cell culture supernatants were included in each experiment with triplicate wells for each experimental group, and were cultivated for a further 48 h. Then, the resulting cell culture supernatants were again collected, and fresh medium supplemented with 10% CCK-8 solution was added thereto. Incubation for an additional 3 h was carried out. Thereafter, the absorbance of the medium was measured at 450 nm wavelength, and the inhibitory rate of cell proliferation by test compound was calculated according to the equation below:

$$R (\%) = 1 - (A_{experiment} - A_{blank})/(A_{control} - A_{blank})$$

in which R is the inhibitory rate of cell proliferation by test compound, $A_{experiment}$ is the absorbance value (450 nm) of the cells in the presence of test compound, $A_{control}$ is the absorbance value (450 nm) of control cells without treatment by test compound, and $A_{blank}$ is the absorbance value (450 nm) of the blank which does not contain the cells.

The results are shown in Table 2.

TABLE 2

$IC_{50}$ of test compounds for proliferation of L929 cell lines

| Code | $IC_{50}$ (µM) |
|---|---|
| T3 | >50 |
| 1 | >50 |
| 2 | >50 |
| 3 | >50 |
| 4 | >50 |
| 5 | >50 |
| 6 | >50 |
| 7 | >50 |
| 8 | >50 |
| 9 | >50 |
| 10 | >50 |
| 11 | >50 |
| 12 | >50 |
| 13 | >50 |
| 14 | >50 |
| 15 | >50 |
| 16 | |
| 17 | >50 |
| 18 | >50 |
| 19 | >50 |
| 20 | >50 |
| 21 | >50 |
| 22 | >50 |
| 23 | >50 |
| 24 | >50 |
| 25 | >50 |
| 26 | >50 |
| 27 | >50 |
| 28 | >50 |
| 29 | >50 |
| 30 | >50 |
| 31 | >50 |
| 32 | >50 |
| 33 | >50 |
| 34 | >50 |

TABLE 2-continued

IC$_{50}$ of test compounds for proliferation of L929 cell lines

| Code | IC$_{50}$ (μM) |
|---|---|
| 35 | >50 |
| 36 | >50 |
| 37 | >50 |
| 38 | >50 |
| 39 | >50 |
| 40 | >50 |
| 41 | >50 |
| 42 | >50 |
| 43 | >50 |
| 44 | >50 |
| 45 | >50 |
| 46 | >50 |
| 47 | >50 |
| 48 | >50 |
| 49 | >50 |
| 50 | >50 |

T3 listed in Table 1 above was used as a positive control. The results show that the compounds all had IC50 values of greater than 50 μM, which indicates that the compounds of the present disclosure showed no toxic effect on normal cells. This provides a further advantage of the compounds over prior art substituted pyridazinones, and provides basis for pharmacological studies of the compounds in individuals with NASH and for druggability assessment thereof.

3) Test of Metabolic Stability in Human and Rat Hepatic Microsomes

Microsomal incubations were performed in 0.05 M Tris-KCl buffer (pH 7.4) in the presence of test compound dissolved in DMSO at a series of concentrations, rat liver microsomes (RLMs) (S9 or human liver microsomes (HLMs)), rat liver cytoplasms (RLCs) (human liver cytoplasms (HLCs, 0.5 mg/mL)), 1.3 mM β-nicotinamide adenine dinucleotide phosphate sodium salt (NADP), 3.3 mM D-glucose-6-phosphate disodium salt (G-6-P), 0.4 units/mL glucose-6-phosphate dehydrogenase (G-6-PDH, type XII), and 3.3 mM MgCl$_2$. The volume of the organic solvents was not more than 1% by volume with respect to the reaction system. After a preincubation of the mixture in a rotating mixer at 37° C. and 850 rpm for 3 min, hepatic microsomes were added to initiate incubation reactions, which were conducted at 37° C. for 30 min, 60 min, or 90 min, respectively. After the incubations were complete, the reactions were terminated by addition of an equal volume of ice cold acetonitrile, followed by addition of 20 μL of a 1 mg/mL solution of genipioside (internal standard) in methanol and then by centrifugation at 10,000 rpm for 10 min to precipitate protein. The precipitated protein was blown dry with nitrogen at 40° C. and then dissolved in 100 μL of methanol, which was used as mobile phase. 10 μL of the solution was sampled and analyzed by HPLC.

The results are shown in Table 3.

TABLE 3

Half-life and clearance (by metabolic pathways) of test compounds in/from human liver microsomes

| Code | T ½ (min) | CLint (μL/min/mg) |
|---|---|---|
| MGL-3196 | <400 | 2.21 |
| 6 | 980 | 0.18 |
| 7 | 1100 | 0.12 |
| 24 | 870 | 0.452 |

The results show that the test compounds exhibited greater metabolic stability in HLMs than MGL-3196. That is, these compounds had improved metabolic stability and can be advantageous in terms of druggability.

The descriptions above are just preferred embodiments of the disclosure, which, however, are not intended to limit the scope of the disclosure. Accordingly, those skilled in the art will recognize that various modifications and substitutions of the embodiments described herein can be made without departing from the scope and spirit of the disclosure.

What is claimed is:

1. A substituted pyridazinone compound selected from the group consisting of:

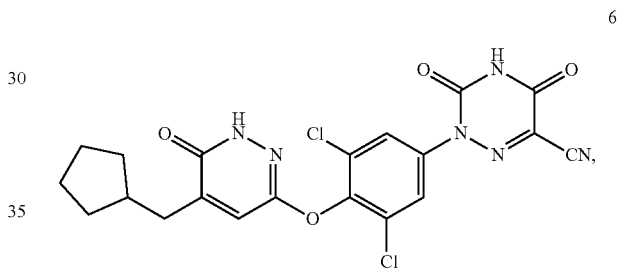

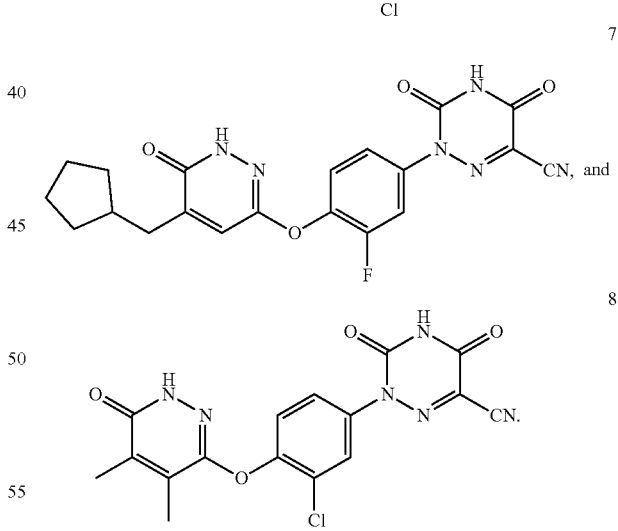

2. A pharmaceutical composition comprising the substituted pyridazinone compound according to claim 1 or a pharmaceutically acceptable salt of the substituted pyridazinone compound, and a pharmaceutically-acceptable carrier or excipient.

* * * * *